United States Patent
Zellmer et al.

(10) Patent No.: US 11,471,297 B2
(45) Date of Patent: Oct. 18, 2022

(54) SYSTEM AND METHOD TO ALTER ELECTRICALLY STIMULATED BONE GROWTH THROUGH ELECTRODE SELECTION

(71) Applicant: Intelligent Implants Limited, Cork (IE)

(72) Inventors: Erik Robert Zellmer, Gottenburg (SE); Juan Sebastian Pardo, Houston, TX (US)

(73) Assignee: Intelligent Implants Limited, Cork (IE)

( * ) Notice: Subject to any disclaimer, the term of this patent is extended or adjusted under 35 U.S.C. 154(b) by 309 days.

(21) Appl. No.: 16/592,566

(22) Filed: Oct. 3, 2019

(65) Prior Publication Data

US 2020/0108252 A1 Apr. 9, 2020

Related U.S. Application Data

(60) Provisional application No. 62/740,839, filed on Oct. 3, 2018, provisional application No. 62/740,853, filed on Oct. 3, 2018.

(51) Int. Cl.
*A61F 2/44* (2006.01)
*A61N 1/05* (2006.01)
(Continued)

(52) U.S. Cl.
CPC .......... *A61F 2/4455* (2013.01); *A61N 1/0551* (2013.01); *A61N 1/326* (2013.01);
(Continued)

(58) Field of Classification Search
CPC ............ A61F 2/4455; A61F 2002/2821; A61F 2310/00149; A61F 2/482;
(Continued)

(56) References Cited

U.S. PATENT DOCUMENTS 1,029,831 A 6/1912 Teed
3,842,841 A 10/1974 Brighton et al.
(Continued)

FOREIGN PATENT DOCUMENTS

EP 3789079 A1 3/2021
WO 2013188380 A1 12/2013
WO 2014089299 A3 10/2014

OTHER PUBLICATIONS

Laughner Ji, et al. (2013) A Fully Implantable Pacemaker for the Mouse: From Battery to Wireless Power. PLOS One 8(10): e76291. https://doi.org/10.1371/journal.pone.0076291, Oct. 23, 2013.
(Continued)

*Primary Examiner* — Yashita Sharma
*Assistant Examiner* — Melissa A Hoban
(74) *Attorney, Agent, or Firm* — Alpine Patents LLC; Brian Van Osdol

(57) ABSTRACT

A system and method for altering bone growth on and within an orthopedic implant comprising an implant body, wherein the implant body comprises an exterior surface and an interior surface defining an internal cavity of the implant body, a plurality of electrodes, wherein each electrode is at least partially embedded in the implant body, and comprises at least, a first set of the plurality of electrodes 116, composed of a first material, and a second set of the plurality of electrodes, composed of a second material; and a control system, comprising a processor and circuitry that connects to the plurality of electrodes, wherein the processor, through operating modes, provides machine instructions to control direction and magnitude of current traveling through each electrode from the plurality of electrodes; and a power system, comprising a power source and circuitry that provides electrical power for function of the plurality of electrodes.

17 Claims, 15 Drawing Sheets

(51) Int. Cl.
  *A61N 1/32* (2006.01)
  *A61N 1/378* (2006.01)
  *A61N 1/36* (2006.01)
  *A61F 2/28* (2006.01)
  *A61L 27/06* (2006.01)

(52) U.S. Cl.
  CPC ......... *A61N 1/36062* (2017.08); *A61N 1/378* (2013.01); *A61N 1/3787* (2013.01); *A61F 2002/2821* (2013.01); *A61F 2310/00149* (2013.01); *A61L 27/06* (2013.01)

(58) Field of Classification Search
  CPC ...... A61F 2002/30593; A61F 2002/448; A61F 2/4465; A61F 2/447; A61N 1/0551; A61N 1/326; A61N 1/36062; A61N 1/378; A61N 1/3787; A61L 27/06
  See application file for complete search history.

(56) References Cited

U.S. PATENT DOCUMENTS

| | | | |
|---|---|---|---|
| 4,175,565 A * | 11/1979 | Chiarenza | A61B 17/58 433/174 |
| 4,313,438 A | 2/1982 | Greatbatch | |
| 4,690,144 A | 9/1987 | Rise et al. | |
| 4,690,166 A | 9/1987 | Howeth | |
| 5,056,518 A * | 10/1991 | Pethica | A61N 1/08 607/2 |
| 5,358,514 A * | 10/1994 | Schulman | A61N 1/372 607/118 |
| 5,441,527 A * | 8/1995 | Erickson | A61N 1/05 607/116 |
| 5,458,627 A * | 10/1995 | Baranowski, Jr. | A61N 1/205 607/51 |
| 5,565,005 A | 10/1996 | Erickson et al. | |
| 5,974,342 A | 10/1999 | Petrofsky | |
| 5,989,289 A | 11/1999 | Coates et al. | |
| 6,120,502 A | 9/2000 | Michelson | |
| 6,292,699 B1 | 9/2001 | Simon et al. | |
| 6,400,990 B1 | 6/2002 | Silvian | |
| 6,582,467 B1 | 6/2003 | Teitelbaum et al. | |
| 6,605,089 B1 | 8/2003 | Michelson | |
| 7,104,986 B2 | 9/2006 | Hovda et al. | |
| 7,309,338 B2 | 12/2007 | Cragg | |
| 7,324,852 B2 | 1/2008 | Barolat et al. | |
| 7,359,755 B2 | 4/2008 | Jones et al. | |
| 7,455,672 B2 | 11/2008 | Michelson | |
| 7,578,819 B2 | 8/2009 | Bleich et al. | |
| 7,935,116 B2 | 5/2011 | Michelson | |
| 8,014,873 B2 | 9/2011 | Jones et al. | |
| 8,078,282 B2 | 12/2011 | Nycz | |
| 8,078,283 B2 | 12/2011 | Cowan et al. | |
| 8,206,387 B2 | 6/2012 | Michelson | |
| 8,463,401 B2 | 6/2013 | Jones et al. | |
| 8,718,777 B2 * | 5/2014 | Lowry | A61N 1/0534 607/45 |
| 8,740,879 B2 | 6/2014 | Martinson et al. | |
| 8,771,360 B2 | 7/2014 | Jimenez et al. | |
| 8,838,249 B2 | 9/2014 | Nycz | |
| 8,903,502 B2 | 12/2014 | Perryman et al. | |
| 10,292,831 B2 | 5/2019 | Zellmer et al. | |
| 10,617,880 B2 | 4/2020 | Zellmer et al. | |
| 2003/0078634 A1 | 4/2003 | Schulman et al. | |
| 2004/0249373 A1 * | 12/2004 | Gronemeyer | B05D 1/60 606/41 |
| 2005/0033393 A1 | 2/2005 | Daglow | |
| 2005/0216702 A1 | 9/2005 | Paolucci et al. | |
| 2007/0250045 A1 | 10/2007 | Trieu | |
| 2008/0039901 A1 * | 2/2008 | Kronberg | A61N 1/326 607/50 |
| 2008/0294211 A1 | 11/2008 | Moffitt | |
| 2008/0300660 A1 | 12/2008 | John | |
| 2009/0062886 A1 | 3/2009 | O'Handley et al. | |
| 2010/0168829 A1 * | 7/2010 | Schwartz | A61N 1/378 607/116 |
| 2010/0204551 A1 | 8/2010 | Roche | |
| 2010/0292756 A1 * | 11/2010 | Schneider | A61N 1/326 607/50 |
| 2011/0009728 A1 * | 1/2011 | Schouenborg | A61N 1/0551 600/373 |
| 2011/0087315 A1 * | 4/2011 | Richardson-Burns | B29C 67/02 607/116 |
| 2011/0092948 A1 | 4/2011 | Shachar et al. | |
| 2011/0301716 A1 * | 12/2011 | Sirivisoot | A61L 27/50 623/23.53 |
| 2013/0150970 A1 | 6/2013 | Thaiyananthan | |
| 2013/0165991 A1 * | 6/2013 | Kim | A61N 1/0558 607/46 |
| 2013/0296940 A1 | 11/2013 | Northcutt et al. | |
| 2014/0114382 A1 | 4/2014 | Kim | |
| 2014/0133123 A1 | 5/2014 | Prasannakumar et al. | |
| 2014/0275847 A1 | 9/2014 | Perryman et al. | |
| 2014/0277260 A1 | 9/2014 | Khalil et al. | |
| 2014/0371823 A1 | 12/2014 | Mashiach et al. | |
| 2015/0018728 A1 | 1/2015 | Gross et al. | |
| 2015/0134061 A1 | 5/2015 | Friis et al. | |
| 2015/0187320 A1 | 7/2015 | Ren | |
| 2016/0270927 A1 | 9/2016 | Zellmer et al. | |
| 2017/0007420 A1 * | 1/2017 | Stevenson | A61B 5/076 |
| 2017/0157407 A1 | 6/2017 | Zellmer et al. | |
| 2017/0246448 A1 * | 8/2017 | Lenoble | A61L 27/306 |
| 2018/0208992 A1 | 7/2018 | Langevin et al. | |
| 2018/0310964 A1 * | 11/2018 | Stevenson | A61N 1/326 |
| 2019/0224022 A1 | 7/2019 | Zellmer et al. | |
| 2019/0247198 A1 | 8/2019 | Zellmer et al. | |
| 2020/0107940 A1 | 4/2020 | Murphy et al. | |
| 2020/0297513 A1 * | 9/2020 | Zellmer | A61B 5/4851 |

OTHER PUBLICATIONS

WIPO European Searching Authority, "PCT2016000482 WO Search and Opinion", dated Jul. 7, 2016.

* cited by examiner

Electrode

Spacer

Providing a plurality of electrodes with the electrodes made of at least two material constructions S110

Positioning of electrodes S120

Creating a polarity within a subset of the electrodes S130

FIGURE 15

SYSTEM AND METHOD TO ALTER ELECTRICALLY STIMULATED BONE GROWTH THROUGH ELECTRODE SELECTION

CROSS-REFERENCING TO RELATED APPLICATIONS

This application claims the benefit of U.S. Provisional Application No. 62/740,839, filed on 3 Oct. 2018, and U.S. Provisional Application No. 62/740,853, filed on 3 Oct. 2018, both of which are incorporated in their entireties by this reference.

TECHNICAL FIELD

This invention relates generally to the field of electrically stimulated bone growth, more specifically, to a new and useful system and method to alter bone growth in a specific spatial region using different conducting materials.

BACKGROUND

Spinal fusion is one of the most commonly performed surgical procedures within the US and in Europe. The goal of spinal fusion surgery is to introduce bone growth between two or more vertebrae, fusing them into a single, continuous unit. Spinal fusion surgery is performed in the lumbar, cervical and thoracic regions, and fusions within each region are associated with a different set of complications. Even so, most complications following spinal fusion can be generalized into two broad categories: non-fusions, where the vertebrae are not fused into a singular unit due to insufficient bone formation within the fusion space; heterotopic ossification, where bone growth damages or impinges on tissue causing harm or discomfort to the patient. Examples of heterotopic ossification includes: Anterior osteophyte formation causing mass effect on the esophagus leading difficulty of swallowing (cervical fusions); ossification of the posterior longitudinal ligament; and formation of posterior osteophyte and/or other excessive posterior bone growth pressuring the spinal cord and/or spinal nerves.

Many contemporary spinal fusion hardware and biologics include designs to address the problems associated with non-unions, with little regard to heterotopic ossification. For example, commonly used biologics, particularly recombinant human bone morphogenetic protein (rhBMP-2), have been used to reduce non-fusion rates by increasing bone formation in the fusion space and the volume surrounding it. While clinically proven to decrease non-unions, numerous studies have shown that the biologic causes a host of side effects including but not limited to cancer, tissue swelling, growth of benign tissue, teratogenicity, pathological heterotopic ossification, nerve injury and spinal cord injury. While not all side effects caused by rhBMP-2 are related to heterotopic ossification, many are. As such, the biologic represents an illustrating example of how, nonspecific, unguided osteoinduction can be harmful to a patient and the delicate balance between increasing fusion rates and avoiding heterotopic ossification.

A second method utilized in reducing non-union rates is electrical stimulation. When mechanical stress is exerted on bone, an electric field is created. In the body, this electrical field constitutes a signal causing a physiological response resulting in osteoinduction or osteolysis. Consequently, it is possible to cause osteoinduction or osteolysis by introducing an electrical field in the volume within and surrounding a segment of bone. In volumes where the current density is above a certain threshold, osteoinduction is achieved if the polarity of the field in the region is electronegative while bone in regions where the field is electropositive undergoes osteolysis. However, in many implementations there is a lack of precise control over the regions of electrical stimulation. Thus, there is a need in the field of electrically stimulated bone growth to create a new and useful system and method to alter bone growth through electrode selection. This invention provides such a new and useful system and method

BRIEF DESCRIPTION OF THE FIGURES

FIG. 15 is a flowchart of a method of preferred embodiment.

DESCRIPTION OF THE EMBODIMENTS

The following description of the embodiments of the invention is not intended to limit the invention to these embodiments but rather to enable a person skilled in the art to make and use this invention.

1. Overview

Figure 1:
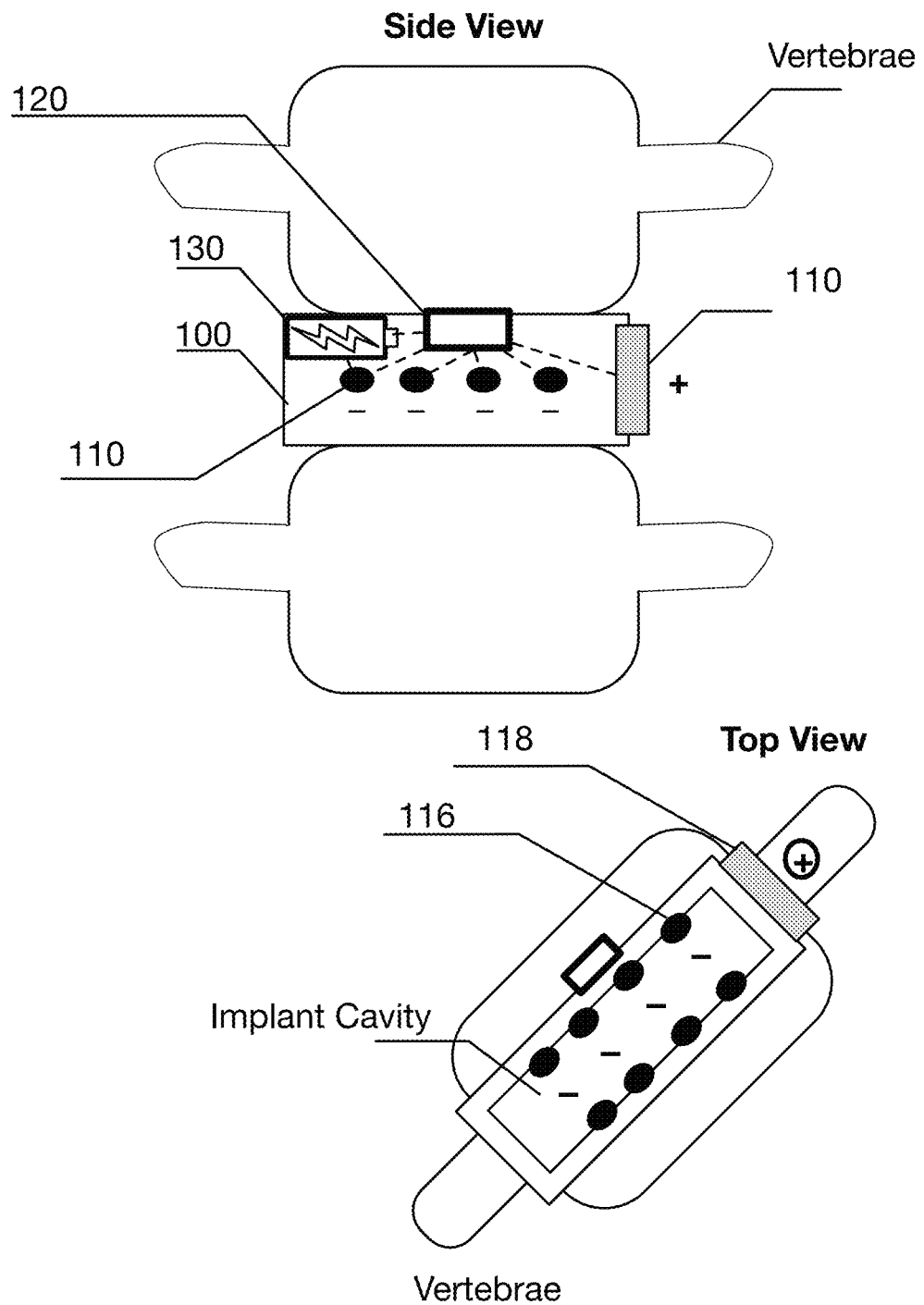
FIG. 1 is a schematic representation of a system of a preferred embodiment.

As shown in FIG. 1, a system and method for altering bone growth on and within an orthopedic implant includes: an implant body; at least two distinct sets of electrodes composed of at least two distinct materials used to stimulate tissue for bone growth; a control system that controls the system components; and a power system that provides power to the system components. The system and method function to alter bone growth to allow more precise control of osteoinduction (bone growth) and osteolysis (bone breakdown) using specific material components as electrodes within a spatial region with respect to an implant. Also, the system and method may allow better control of electrically induced bone growth through static and/or dynamic selection of electrodes of different material types. By implementing complex structured electrodes of distinct material types, control of osteoinduction and osteolysis may be better controlled. Depending on material type, osteoinduction may be induced in an enhanced manner throughout the implant body. Complex multi-structured and/or multi-functional electrodes may additionally allow for better dynamic capability of bone growth in specific regions.

The system and method may be applied to spinal fusion implants. However, the system and method may alternatively be used in other forms of orthopedic implants. In the spinal fusion example, an implant may be implanted in the space between two vertebrae. The implant preferably has a cavity that can function as a "bone-growth" region wherein electrical stimulation from the electrodes, or another source, may induce bone growth.

One potential benefit of the system and method is enhanced control bone growth and bone breakdown. Selection of electrodes of a particular material may enhance desired bone growth behavior and/or diminish undesired bone growth behavior.

A potential benefit of the system and method is that with enhanced control of regions of electrical stimulation, bone growth dynamics may increase the likelihood of a successful spinal fusion. The system and method can be applied to an implant so that regions of osteoinduction and osteolysis are promoted in specific and targeted regions. In one example, the electro-positive electrode is positioned at a removed position on the external surface of an implant.

Another potential benefit comes from using an electrode material that induces just osteoinduction at the electro-negative electrode and the electro-positive electrode, thus minimizing or preventing significant osteolysis and thereby maximizing osteoinduction. Creating an expanded region of bone growth may additionally help increase the success of spinal fusion.

Another potential benefit comes with better dynamic control of bone growth. With a greater range of electrode capability due to complex structured electrodes with selective materials, the system and method may allow greater flexibility in modifying the bone growth regions after implantation. Greater electrode capability may additionally reduce the need for invasive adjustment of electrodes after the initial implantation of the implant.

A potential benefit of the system and method is that with enhanced control of regions of electrical stimulation, bone growth dynamics may increase the likelihood of a successful spinal fusion. The system and method can be applied to an implant so that regions of osteoinduction and osteolysis are promoted in specific and targeted regions. In one example, the anode is positioned at a removed position on the external surface of an implant.

Another potential benefit comes with more uniform osteoinduction. Controlling and maintaining bone growth in a region may lead to greater bone mass densities, thus uniform osteoinduction may lead to the creation of more uniform and stronger bone structure, as opposed bone tissue created by a mix of osteoinduction and osteolysis.

Another potential benefit of the system and method is improved control of bone density and porosity. Increased control of osteoinduction may allow better control of bone formation, and the amount of bone formation, in a given region.

Another potential benefit is that preventing bone growth outside of the desired area of growth reduces the risk of bone growth onto soft tissue. Bone growth onto soft tissue may in fact damage the tissue and/or reduce the function of the tissue. Reducing the risk of damaging soft tissue thus helps minimize negative impacts of bone growth treatment.

The system and method may be implemented with any series of orthopedic implants, preferably in a region of bone growth. The orthopedic implant may itself contain electrodes such that the implant itself induces bone growth dynamics. The system and method may alternatively be implemented with other types of implants, wherein some other mechanism may be responsible for bone growth dynamics.

2. System

As shown in FIG. 1, a system for altering bone growth on or within an orthopedic implant includes: an implant body 100; a plurality of electrodes 110, comprising a first set of electrodes 116 composed of a first material and a second set of electrodes 118 composed of a second material; a control system 120, that controls the activity of each electrode from the plurality of electrodes; and a power system 130, that provides power for the function of the plurality of the electrodes. The system functions as an orthopedic implant that monitors and/or promotes bone growth. In some preferred variations, the system may additionally include a communication system enabling communication of implant components.

In some variations, the system may incorporate the system for altering bone growth on or within an orthopedic implant in an implant device such as the one described in U.S. patent application Ser. No. 15/075,152, filed 19 Mar. 2019, which is hereby incorporated in its entirety by this reference.

In preferred variations the implant body 100 has both an exterior surface and an interior surface that defines an internal cavity. The plurality of electrodes is preferably comprised of at least two distinct sets of electrodes, wherein the first set of electrodes 116 and the second set of electrodes 118 contain at least one electrode. In some variations, each distinct set of electrodes has a distinct material composition. The control system 120 preferably includes a processor and circuitry that connects the control system to the plurality of electrodes 110. The processor may operate in various modes and can include machine instruction configuration that comprises instructions to control direction and magnitude of current traveling through each electrode from the plurality of electrodes.

The implant body 100 of a preferred embodiment functions as a structural element, housing, or holding other implant subcomponents. The implant body 100 is preferably made of non-conductive material, but may be partially conductive. The implant body 100 may structurally serve a medical objective. The shape and form may be of those of other passive medical device implant body such as orthopedic implant devices like cervical plates, monoaxial screws, spinal cages, meshes, and pins. The implant body 100 is preferably integrated with the plurality of electrodes 100 such that electrical stimulation enhances recovery. The medical implant bodies may house some or all circuit elements (e.g., PCB, leads, antennas etc.) included as part of the implantable components. Preferably, the implant body 100 includes integrated electrode sites, which may be distributed across the geometry of the implant body. These integrated electrode sites may be distributed in such a way as to facilitate bone growth and bone reabsorption in distinct regions. In some embodiments, the implant body 100 can be a spinal implant, which may be a spinal cage. A non-exhaustive list of descriptions of typical spinal cages that may be incorporated with the system will follow. As spinal cages may be highly specialized for each individual implementation, all provided spinal cage specifications are provided as typical descriptions of that spinal cage and not presented as a limitation for each spinal cage per se.

The spinal cage variation of the implant body 100 may be made of a polymer, such as PEEK, or it may be made of engineered natural or synthetic bone material, or some other material. The spinal cage generally has an extruded prism geometry with many variations dependent on the specific type of spinal cage. As per a prism, the spinal cage geometry has an external surface comprising: a sufficiently, flat and opposing (e.g., parallel), top and bottom surface; and a more complex outer wall geometry that may be distinct to the specific spinal cage implementation. Herein, opposing characterizes the general geometry of the top and bottom surfaces of the implant without requiring the surfaces to be parallel or flat and may include surfaces defined along intersecting planes. Preferably, the opposing surfaces are defined along planes with angular offset between 0-10 degrees, although the offset may be more. For example, in many implementations, the top and bottom surfaces are skew several degrees to achieve lordosis. As discussed here, the exterior perimeter of the spinal cage is defined as the perimeter along the lateral (i.e. side) wall geometry. The spinal cage can include one or more graft windows, which can be defined as internal implant cavities, wherein these internal implant cavities are defined by the interior surface of the spinal cage. Implant cavities are typically prism shaped with openings in the top and bottom of the spinal cage. The interior surface of the spinal cage thus refers to the lateral walls that define the internal cavities. In some variations, internal cavities may have openings in addition to the top and bottom openings. As desired by implementation, these additional surfaces may also be included as part of the interior surface.

Figure 3A:
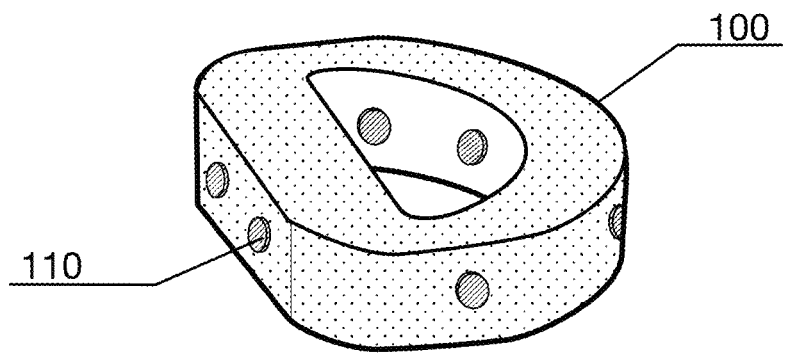
FIG. 3A is a schematic representation of a perspective view of an ALIF cage of a preferred embodiment.

The spinal cage may be incorporated with many geometries including, but not limited to, anterior lumbar interbody fusion (ALIF) cages, transforaminal lumbar interbody fusion (TLIF) cages, posterior lumbar interbody fusion (PLIF) cages, anterior cervical fusion (ACF) cages, lateral cages and/or other suitable types of spinal cages. In some implementations the spinal cage geometry is an extruded prism of some defined form, which generally has a continuous outline and at least one defined internal cavity. More common geometries of the spinal cage may have a rectangular prism resemblance, and may be considered "sufficiently" rectangular to describe components with respect to the sufficiently rectangular implant body 100. The rectangular body comprises a top surface, bottom surface, two shorter sides, and two longer sides; an exterior surface comprising the lateral sides (i.e. the two shorter sides and the two longer sides); and an exterior perimeter comprising circumnavigating the lateral sides. In some variations the rectangular body may have some curvature and geometric features along some or all sides. This curvature may include curved edges of the implant body and/or curvature of the entire rectangular body, as seen in FIG. 3A. The spinal cage may include other design features such as: surface coatings, surgery tool attachment points, teeth, and/or other elements. The spinal cage is preferably composed of a non-conductive polymer, such as PEEK, but may be made of engineered, natural or synthetic bone material, titanium and/or other suitable material or combinations thereof.

Figure 3B:
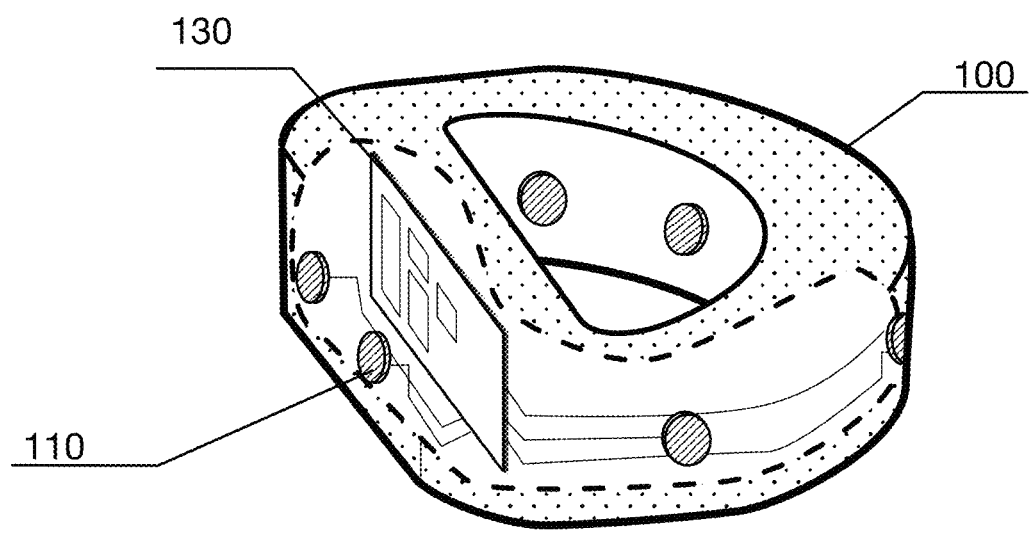
FIG. 3B is a schematic representation of a perspective view of an ALIF cage with an exposed window of internal components.
Figure 4:
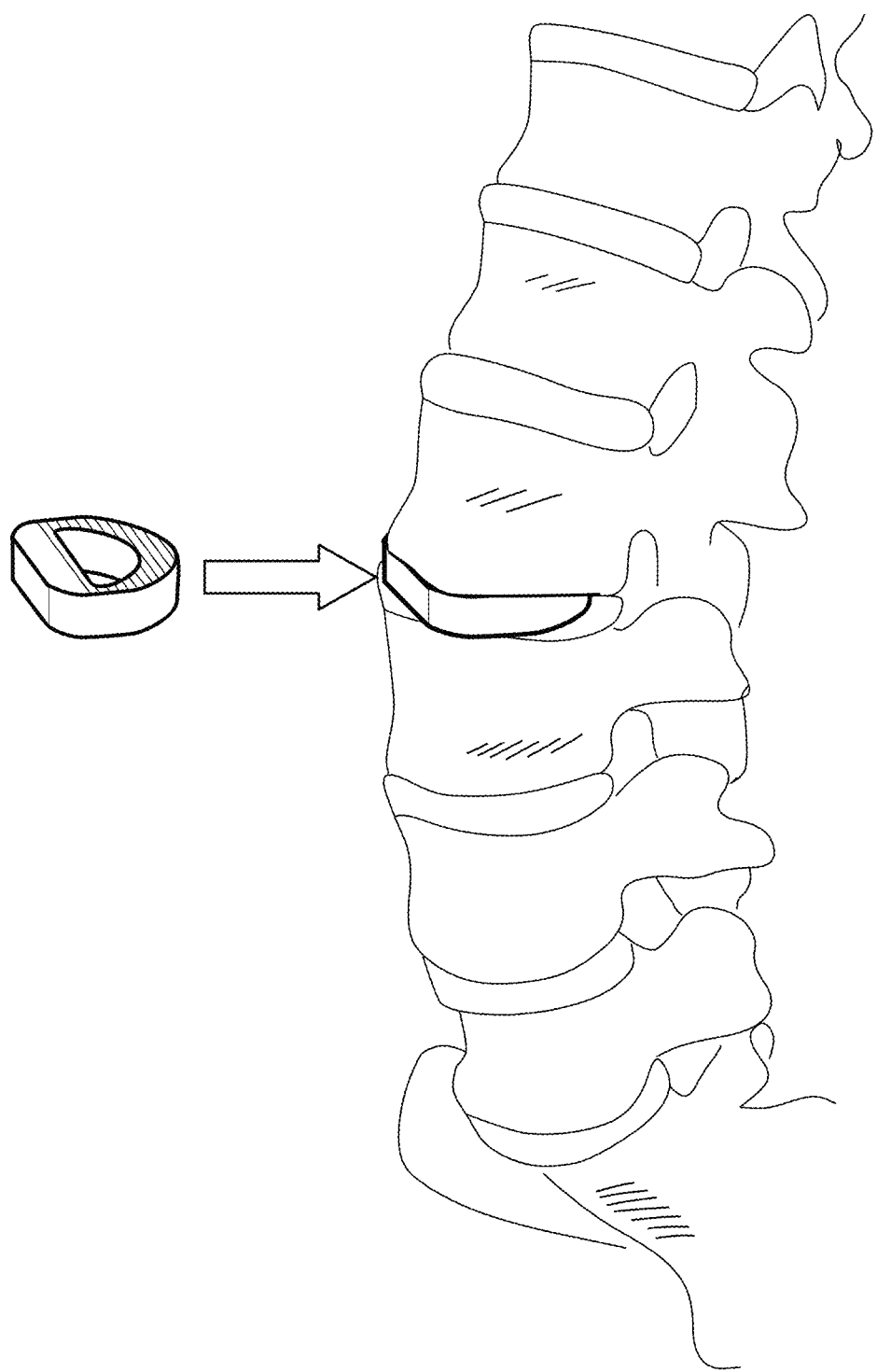
FIG. 4 is an illustration of an implantation of an ALIF cage of a preferred embodiment.
Figure 5:
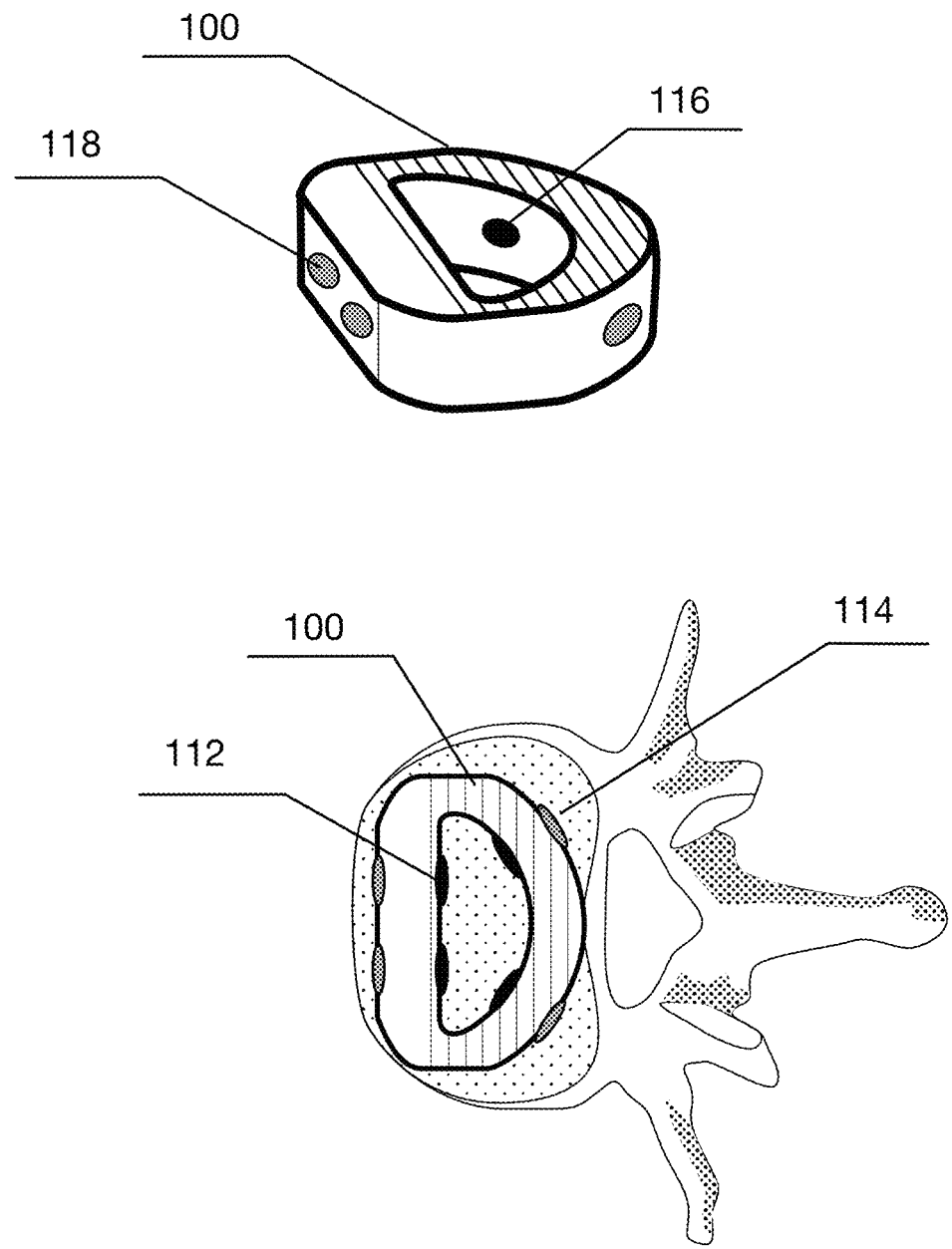
FIG. 5 is an illustration of an ALIF cage implant body of a preferred embodiment.

In some variations, the implant body 100 is an ALIF cage such as shown in FIG. 3 and FIG. 5. The ALIF cage is typically optimized for implantation in the anterior lumbar region of the spinal cord for anterior lumbar interbody fusion, as shown in FIG. 4. The ALIF cage is typically a larger spinal cage implant. Typical ALIF cages may vary between 10×25×35 mm-18×28×39 mm with an interior cavity space that may vary from 2.0 mL-8.0 mL.

Figure 6:
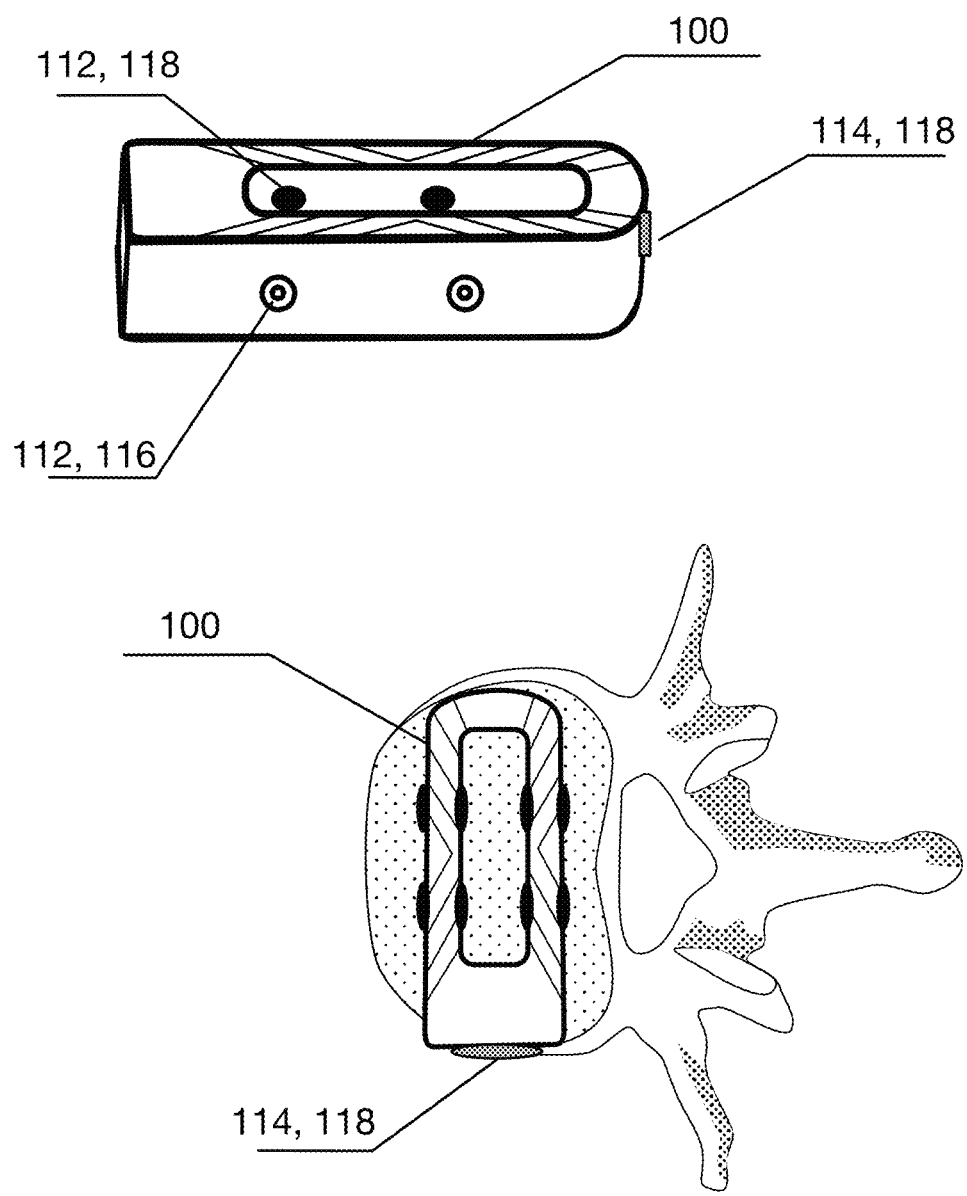
FIG. 6 is an illustration of a lateral cage implant body of a preferred embodiment.
Figure 7:
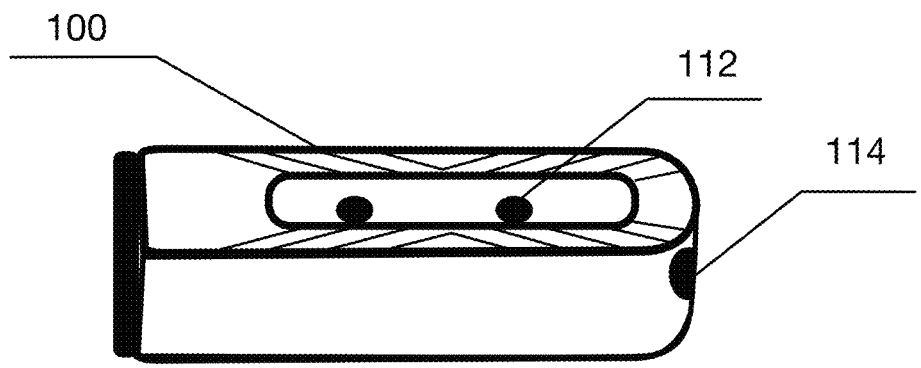
FIG. 7 is an illustration of an alternative lateral cage of a preferred embodiment.
Figure 7:
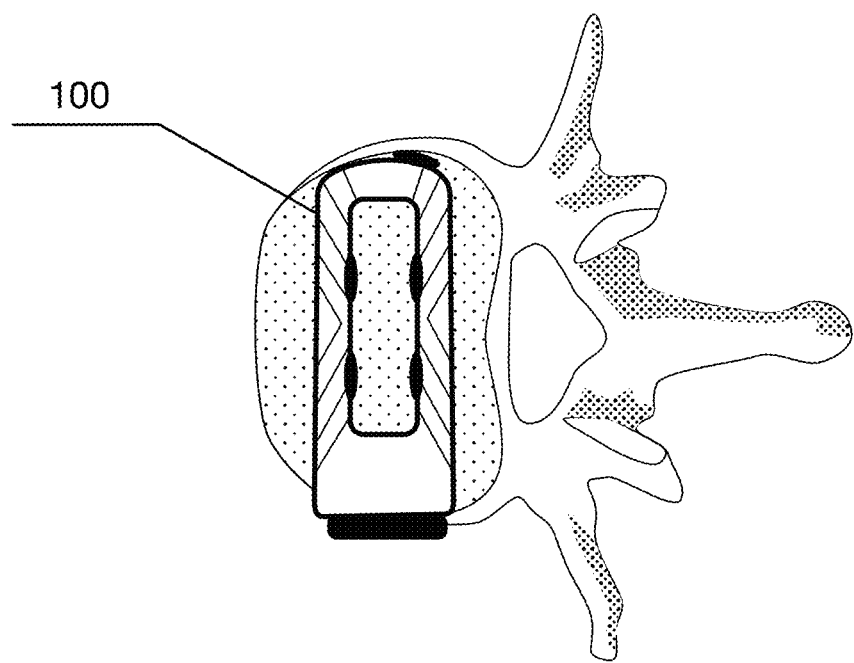
Figure 8:
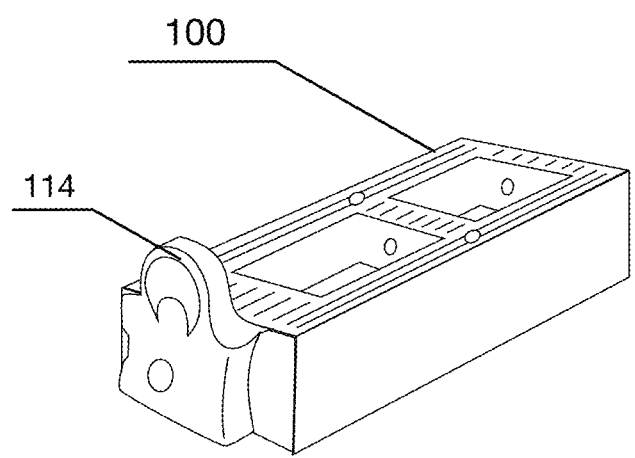
FIG. 8 is an illustration of a lateral cage implant body with external casing of a preferred embodiment.

In some variations, the implant body 100 is a lateral cage. FIGS. 6-8 show typical lateral cages. The lateral cage is typically more rectangularly shaped as compared to the ALIF cage and generally elongated along one dimension with two "end" surfaces being smaller in surface area than the adjacent "elongated" surfaces. Lateral cages may vary between 8×18×30 mm-14×21×60 mm, with an interior cavity space that may vary from 1.4 mL-11.6 mL.

Figure 9:
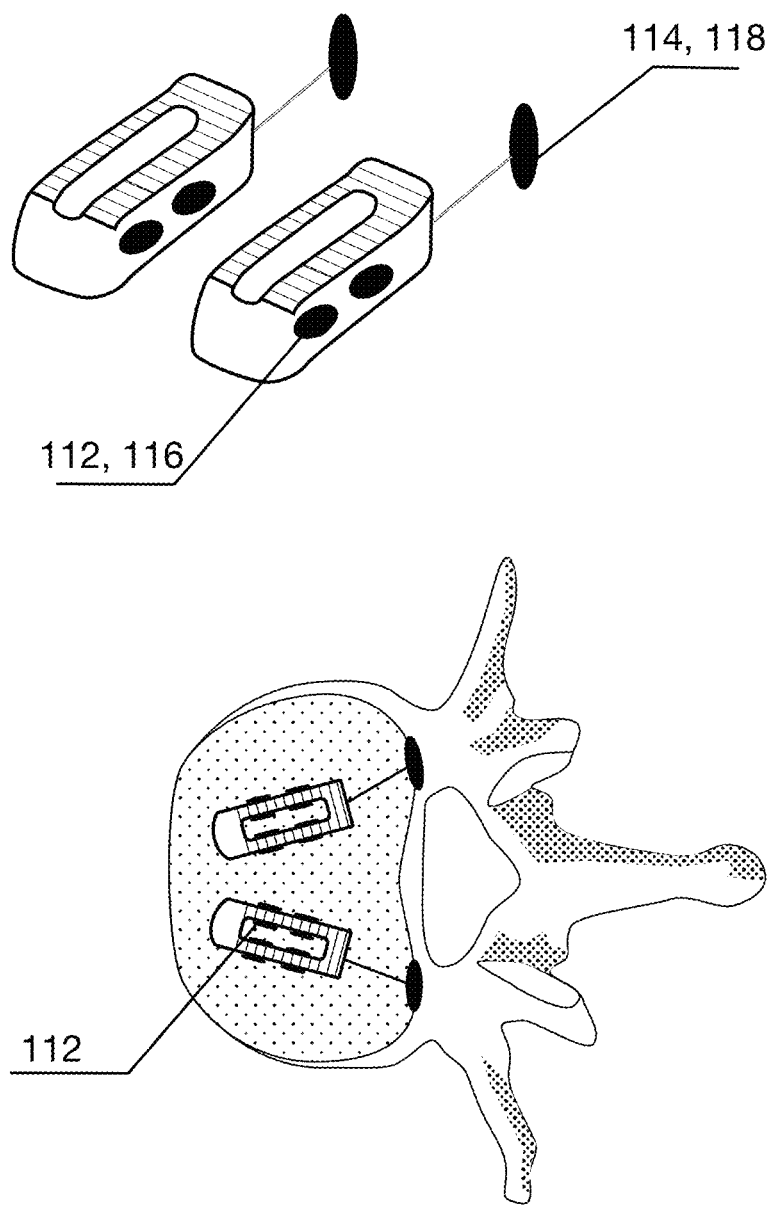
FIG. 9 is an illustration of a PLIF cage implant body of a preferred embodiment.

In some variations, the implant body 100 is a PLIF cage. FIG. 9 shows a typical PLIF cage. The PLIF cage may be a smaller implant body 100 as compared to the ALIF cage, preferably optimized for implantation in the posterior lumbar region of the spinal cord for posterior lumbar interbody fusion, wherein multiple implant bodies may be inserted between a pair of vertebrae. Typical dimensions of the PLIF cage may vary from 6×10×25 mm-16×12×32 mm.

Figure 10:
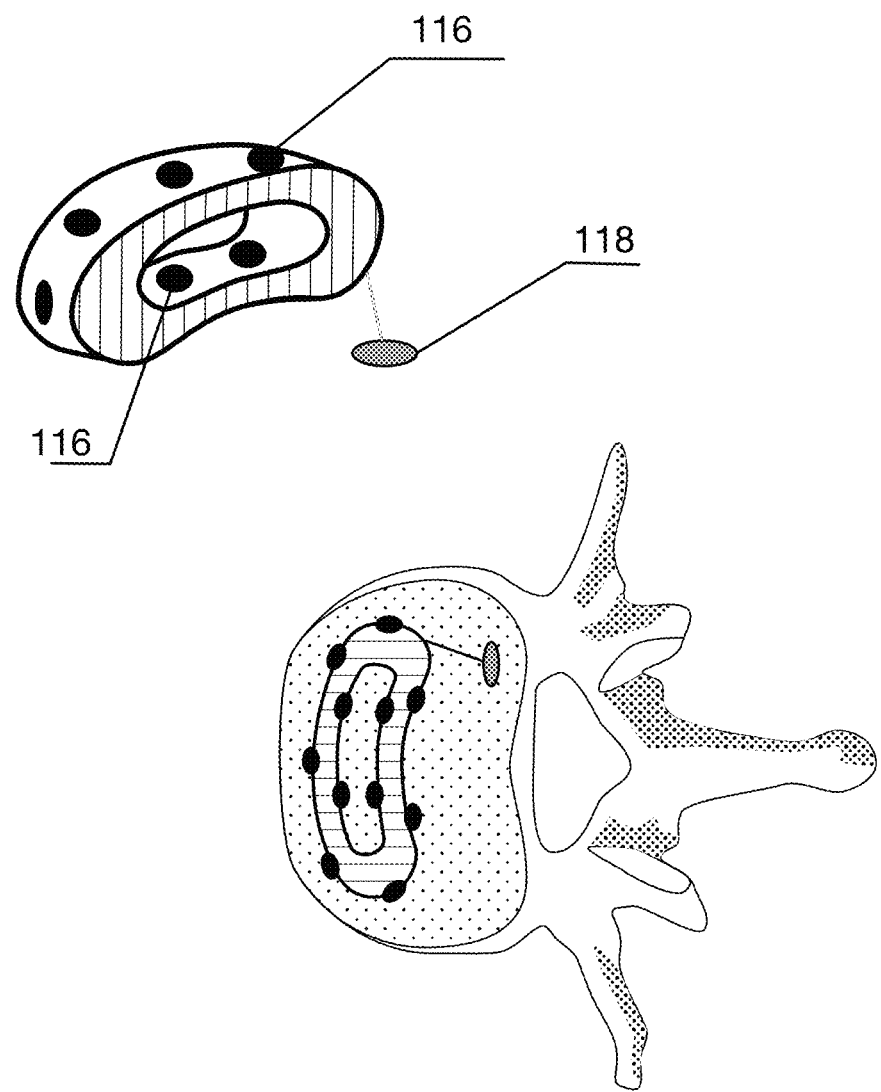
FIG. 10 is an illustration of a TLIF cage implant body of a preferred embodiment.

In some variations, the implant body 100 is a TLIF cage, such as shown in FIG. 10. The TLIF cage is a more rectangular shaped spinal cage that may be used in small incisions for transforaminal lumbar interbody fusion, wherein multiple implants may be inserted between a pair of vertebrae. Typical dimensions of the TLIF cage may vary from 8×10×26 mm-16-11-34 mm. Additionally, the body of the TLIF cage may have a curvature.

In some variations, the implant body 100 is an ACF cage. The ACF cage may be a smaller square-like spinal cage implant inserted preferably between cervical vertebrae. Typical dimensions of the ACF cage may vary from 5×14×11 mm-10×17×13, with an interior cavity space that may vary from 0.20 mL-0.9 mL.

In some variations, the implant body 100 may further include a metal casing, as seen in FIG. 1 and FIG. 8. In some implementations the metal casing may, in part, be conductively isolated from some or all of the plurality of the electrodes. The metal casing, or sub-portions of the metal casing, may additionally function as an electrode as described later.

In alternate variations the implant body may be an orthopedic implant that may or may not have an interior cavity. Orthopedic and non-orthopedic implants that may implement localized bone growth preferably include joint and extremity implants and other connective implants Examples of these implants include: hip implants, knee implants, implant plates, implant nails, and implant screws. The system may additionally be implemented with any other system implant wherein localized charge may be implemented to aid a patient.

The plurality of electrodes 110 of a preferred embodiment function to hold or transfer charge from and to the implant; and to and from the surrounding tissue. An electrode is preferably a conductive element that includes an electrode site (e.g., a conductive pad exposed to body tissue) connected (directly or indirectly) to other implant components (e.g. control system 120 and power system 130). The plurality of electrodes is preferably constructed electrically conductive material. The plurality of electrodes are preferably conductively isolated from the implant body 100 and exposed at a set of distinct electrode sites. The implant sites are preferably exposed electrode sites on or near the interior surface of the implant body 100 and/or on or near the exterior surface of the implant body 100. In some preferred variations, exposed electrode sites may include electrode sites distant from the implant body 100 (e.g. distant to desired bone growth regions). The electrode sites are distributed across the geometry of the implant body 100 in such a way as to facilitate the osteoinduction and osteolysis in desired bone growth regions during a controlled stimulation mode. The electrode site geometry can be configured for differing current density profiles.

In preferred variations electrodes are partially embedded in the implant body 100. These electrodes have at least one "embedded" region within the implant body 100 and at least one "exposed" region (i.e. exposed electrode site), such that the implant body 100 does not completely insulate the electric field generated by the exposed electrode site from external tissue. The exposed electrode site may be along an interior surface (e.g. exposed to an interior cavity or through hole) or an exterior surface (e.g., adjacent to external tissue) of the implant body 100. Embedded regions may include: regions where electrodes are molded into the implant body 100; run through slits and/or holes in the implant body; encased in regions of the implant body; and/or incorporated within the implant body in some other way. Embedded regions may vary significantly dependent on the size and/or shape of the electrode.

Each electrode may be of any desired shape and/or size. In some preferred variations, some electrodes may be wires exposed at defined electrode sites on and/or around the implant body 100. Other examples of electrodes may include, but are not limited to: thin wires, thick wires, layers of distinct wires, sheets, discs, metallic bodies, rings, covering shapes of the implant body 100, covering shapes of the implant body cavity, and/or any combination of the aforementioned examples. In one preferred variation the plurality of electrodes 110 include wires embedded and integrated within the implant body 100. In another variation, the plurality of electrodes 110 include a metal casing on the external surface of the implant body 100.

The exposed electrode sites of electrodes function to enable current transfer to tissue on, or near, the implant body 100. The electrode sites are preferably flush with the surface of the implant body 100 along the interior or exterior cavity of the implant body 100. Alternatively, the exposed electrode sites may protrude from the implant body 100 or be recessed within the implant body 100.

The electrodes of the plurality of electrodes 110 function to hold or transfer charge from and to the implant, to and from the surrounding tissue. Preferably at any given time, charge transfer occurs with a substantially equal charge, being generated at a source and dissipated at a sink; thereby creating an electric field that may induce bone growth, osteoinduction; or bone breakdown, osteolysis. The electrodes are preferably configured for electrical stimulation at, within, and/or around the implant body 100. Electrodes of the system may further be characterized as any material that may function as a cathode or anode of a circuit, allowing current to flow from one to the other.

Electrodes preferably function as anodes and cathodes, i.e. current sources and current sinks respectively; to create regions of bone growth, osteoinduction, and bone breakdown, osteolysis. Thus, the plurality of electrodes 110 are preferably situated such that, at least one electrode has an exposed electrode site in a "bone growth" region, to induce osteoinduction or osteolysis. As desired, the system may have multiple bone growth regions. Dependent on implementation, circumstances regarding the current status of bone growth, and potentially other factors, the desired activity in the bone growth region may change over time. Thus, a specific bone growth region may at times be a region for osteoinduction, osteolysis, or no activity. In preferred variations, wherein the implant body 100 contains an internal cavity, the internal cavity is preferably a bone growth region. In alternate variations, the internal cavity is not a bone growth region.

Each electrode from the plurality of electrodes no is preferably enabled for independent function. Alternatively, sets of electrodes are enabled to function independently as a set (e.g. the first set of electrodes 116 may function independently as a group). Independent function enables precise control of current through each electrode such that the direction and magnitude of current through each electrode may be individually determined and set, as desired. Additionally in some preferred variations, the type of current can also be independently controlled (e.g. direct current, or alternating current).

In some alternate variations, electrode function has limited and/or fixed operation. For example, the system may have a "fixed" source, wherein one set of electrodes may only function as a current source, while another set of electrodes may function only as a current sink.

Each electrode from the plurality of electrodes 110 may additionally be made of different materials. Electrodes are preferably made of metallic compounds and/or other type(s) of material that readily conduct electricity and are biologically non-toxic. Examples of electrode material may include, but are not limited to, platinum (Pt), titanium (Ti), iridium (Ir), oxidized iridium, and titanium nitride. Alternating current (AC) or direct current (DC) impedance of different electrode materials may be significantly different. Using different materials for distinct electrodes, functioning as the electro-negative electrode and/or the electro-positive electrode, may allow using larger (or smaller) electrical potentials to pass faradic or non-faradic current through an electrode. For example, for electrodes of a given surface area, the DC impedance of a cathode/anode pair constructed using titanium will be higher than that of a pair constructed using platinum, for electrode sizes and currents appropriate for electrical stimulation of bone. In addition, the DC impedance of titanium anodes may further increase due to the metal readily oxidizing which is less of a concern for platinum electrodes. More generally, the externally generated potential (electrical potential supplied actively using a circuit) that needs to be applied between electrodes when using different materials to drive a desired current varies greatly depending on: the content and concentration of ions in the fluid that the electrodes are in contact with, the materials themselves, material of the anode, material of the cathode, and/or other suitable factors. As such, for some electrode material choices, very little or no potential may be required to pass current between the anode and the cathode.

Since power is the product of current and electrical potential ($P=V*I$), the choice of materials making up the anodes and cathodes may greatly impact the amount of power that needs to be supplied by the power system in order to cause osteoinduction/osteolysis. This is of special concern in implantable systems where power required to drive current between the electrodes is provided wirelessly since it is difficult to transmit large powers over large distances. Power requirements can impact at what depth a system can be implanted where a system that utilizes anode/cathode materials. For example, a system with anode/cathode materials where small potentials are applied over the cathodes/anodes to drive a desired current may be implanted deeper into a patient compared to a system that utilizes anode/cathode materials where larger potentials are preferably used to drive the same current since the latter requires more power. A greater power consumption also requires larger power sources, which may affect the bulk of the implant and/or power system.

Additionally, certain types of electrode materials may allow for distinct types of bone growth dynamics. In one example, osteoinduction may occur at both the cathode and the anode electrodes where both the cathode and the anode electrodes are constructed from platinum. In an alternate example, where cathode electrodes are constructed of platinum and anode electrodes are constructed of titanium, osteoinduction may occur in proximity of the cathode electrodes, while osteolysis may occur in proximity of the anode electrodes. Thus choosing the appropriate material type for a specific utilization may play a significant role in desired bone growth activity.

The plurality of electrodes no may comprise of distinct sets of electrodes. In one preferred variation, a first set of electrodes 116 is constructed with a first material and at a second set of electrodes 118 is constructed of a second material. As described before, the sets of electrodes constructed of a certain material may function to improve bone growth activity. The first material is preferably different from the second material. In some variations, additional the plurality of electrodes 110 may comprise of additional distinct sets of electrodes made of distinct materials (e.g. a third and fourth set of electrodes). In one example, wherein the plurality of electrodes comprises of two sets of electrodes, a first set of electrodes 116 may be constructed from titanium while a second subset of electrodes may be constructed from platinum.

In some preferred variations, electrodes may be composed of multiple distinct regions, wherein each region is composed of a material distinct from all regions physically adjacent to it. That is, an electrode may have multiple regions. These multiple regions may or may not be exposed at electrode sites. Each region has a composition distinct from all adjacent regions of the same electrode. Multiple regions may enable the electrode to have additional or improved functionality. In one preferred example, the first set of electrodes 116 includes at least one electrode comprised of two distinct regions composed of two different materials; one region is composed of the first material and a distinct region composed of a different material. In one implementation, the first material is chosen to function better as a source and the different material is chosen to function better as a sink for the purposes of bone growth.

Figure 12:
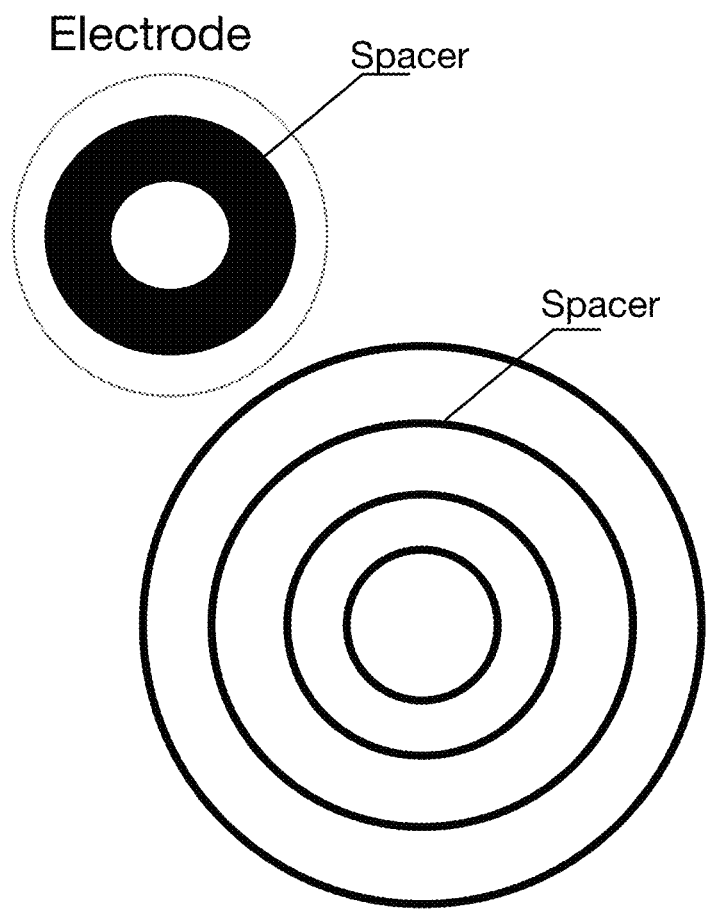
FIG. 12 is an schematic representation of an multi-component electrode of a preferred embodiment.

In a similar variation, as shown in FIG. 12, the electrode may further have an additional, third, distinct region. This third region may be an insulating layer between the first and the second region. A distinct region is preferably conductively isolated from other regions of an electrode within a connecting circuit that is conductively connected to the control system. For example, a spacer or insulator may separate two distinct regions.

Figure 14:
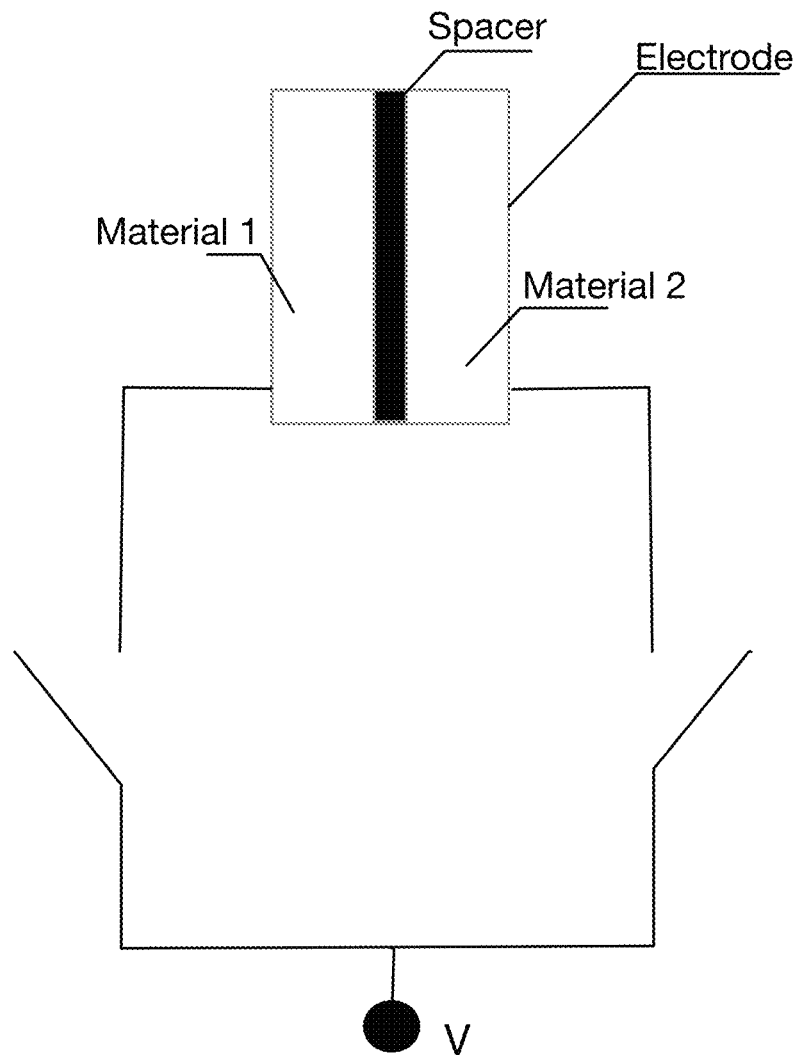
FIG. 14 is a second alternate schematic representation of a multi-component electrode of a preferred embodiment.

In variations where an electrode is comprised of more than one region, the electrode preferably includes a switch. The switch is preferably conductively coupled to the electrode and functions to enable (or disable) functionality of each distinct region of the electrode. The switch may be a digital switch, wherein the switch is or includes a processor and/or microprocessor or any programmable electronic component. The switch may alternatively be an analog switch using discrete components such as one or more transistor circuits, a multiplexor, switch PCB packaged electrical component, and/or set of CMOS packaged electrical components. In the previous example for a two region electrode, the electrode may "switch" (e.g. through the control system) between active regions of the electrode to optimally function as a current source or sink as required; and thus switch between sending a current through the first material and receiving a current through the different region. In one preferred example of an electrode comprising two distinct regions, the electrode comprises a circuit component with a switch, such that the first material region and the different material region of the electrode are parallel components of the circuit, and the switch enables the current to selectively flow only through one of the two regions. In alternate preferred example, as shown in FIG. 14, the electrode comprises two switches thus enabling current to flow through both regions simultaneously.

In one variation of an electrode, wherein the electrode is a two-layer wire, each electrode of the first set of electrodes 116 may have a platinum region on the exterior (i.e. a hollow cylindrical layer composed of platinum), and a titanium region (i.e. a central cylindrical layer composed of titanium). Alternatively titanium may be on the exterior and platinum on the interior. Additionally, the electrode may be a multi-layer wire composed of the central cylindrical layer, the second "hollow" cylindrical layer surrounding the central cylindrical layer, and one or more additional cylindrical layer(s) surrounding the prior hollow cylindrical layer. In one implementation, as described before, the middle layer may be a spacer to insulate the inner and outer layer. As shown in FIG. 12, an electrode wire may be constructed of as many layers as desired. In one preferred implementation of the multi-layer wire, the central cylindrical layer and each alternating layer is composed of a conducting material (i.e. layer 1, layer 3, etc.) wherein each alternating layer after the central cylindrical layer comprises an insulating layer composed of electrically insulating material (i.e. layer 2, layer 4, etc.).

Electrodes may alternatively be constructed of multiple distinct materials organized differently. For example, a multi-region electrode may be made of distinct materials that are layered in sheets, coiled about each other, or lined up next to each other.

Figure 13:
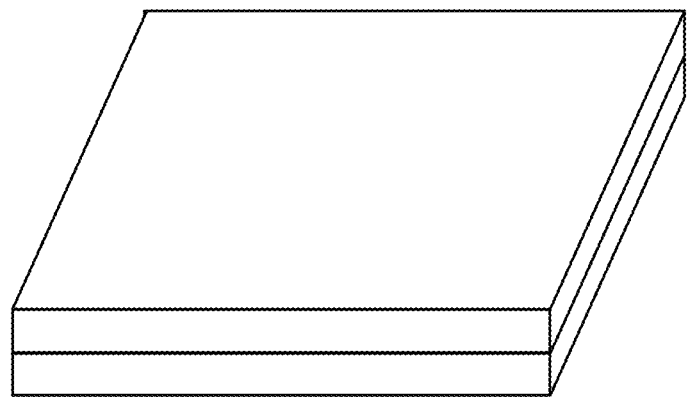
FIG. 13 is an alternate schematic representation of a multi-component electrode of a preferred embodiment.
Figure 13:
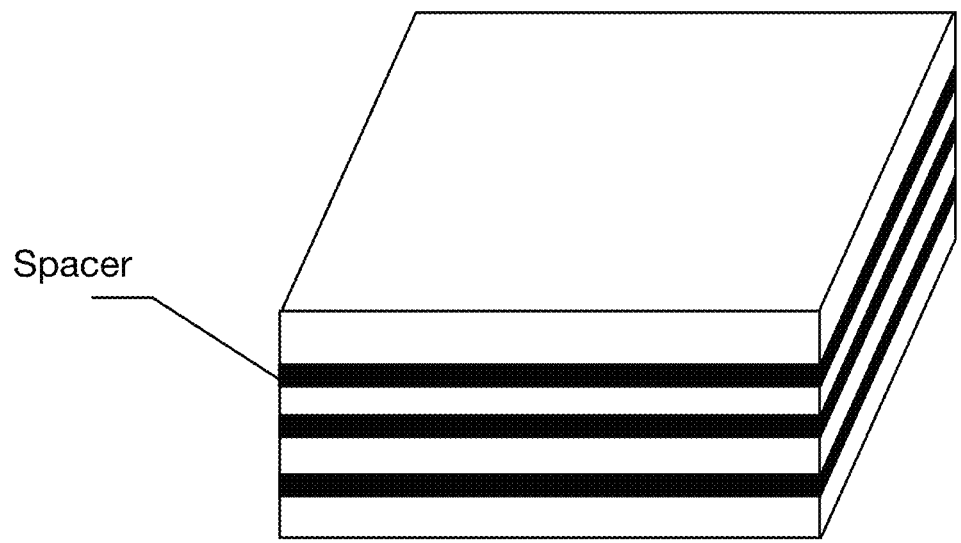

In one example of at least one electrode from the first set of electrodes 116 as a two-layer electrode pad, as shown in top of FIG. 13. Examples of an electrode pad may include an electrode plate on the surface of the implant body 100 or an electrode lead exposed in adjacent tissue. The electrode comprises a two-layer conducting sheet, comprising a flat sheet of the first material (e.g. platinum) and a flat sheet composed of the different material (e.g., titanium) stacked upon the first material covering part of the material. For a multi-layer sheet, as shown on the bottom of FIG. 13, each additional layer comprises a flat sheet layer stacked upon a prior flat sheet, wherein each the additional flat sheet is composed of a distinct material as compared to its prior flat sheet. As described for the wire, multiple layers may be stacked on as desired, with or without alternating insulating layers.

In a second example, a two-layer electrode may comprise of the first material (e.g. platinum) that is shaped in any desired fashion, and then coated in the different material (e.g. titanium).

Electrodes constructed of multiple types of materials may allow for dynamic operating modes, wherein the electrode may switch operation from one material to another material.

That is, a single electrode may switch from one material functionality to another material functionality as deemed fit (e.g. by the control system 120). For example an electrode comprised of a platinum and titanium layer, may activate the titanium active mode and thus the titanium layer of the electrode may pass current while the platinum layer stays uncharged. Alternatively the platinum layer may pass current while the titanium layer stays inactive. Alternatively, both layers may become active or inactive concurrently. Preferably, the control system 120 dynamically controls the mode of activation of electrodes with multiple electrical stimulation modes. For example, a single electrode function may be able to use a digitally controlled switch to selectively activate different material constructions as shown in FIG. 14.

Electrodes constructed of multiple types of material may additionally have a dual operating mode (multi-operating modes), wherein distinct layers of the electrode simultaneously function in a distinct manner. That is, an electrode exposed at a singly positioned electrode site may have distinct sections (e.g. a platinum and a titanium section) where one section functions as an electro-negative electrode and another section functions as an electro-positive electrode. In one implementation where potentially precise and localized bone growth is required, dual operating mode electrodes may have an electro-negative exterior and an electro-positive interior creating a short range electric field between the two layers allowing for precisely controlled osteoinduction and/or osteolysis. In one preferred variations, these regions may effectively form segments of a circuit wherein a switch (preferably controlled by the control system 120) may enable switching between one region and the other region. In another preferred variation, the switch may additionally enable switching such that both layers function simultaneously.

The plurality of electrodes 110 preferably includes at least one electrode proximal to the bone growth region, i.e. a set of primary electrodes 112. Primary electrodes 112 function to induce osteoinduction and/or osteolysis in the bone growth region as desired. Primary electrodes 112 may comprise of a first set of electrodes 116 or a second set of electrodes 118. In a configuration for primarily promoting osteoinduction, primary electrodes 112 are configured to typically function as cathodes (current sinks). The set of primary electrodes 112 is preferably proximal to the bone growth region and may be positioned inside, on, or around the desired region of bone growth. In preferred variations, wherein the implant body 100 contains integrated electrode sites, a subset of primary electrodes 112 may be located on or within the integrated electrode sites of the implant body 100. Primary electrodes 112 may have any desired size or shape as generally described for electrodes (e.g. thin, thick, straight wire, spiral wire, ring, disc, covering shape, etc.).

The plurality of electrodes 110 may further include at least one electrode distal to the bone growth region, i.e. a set of secondary electrodes 114. In some variations, the set of secondary electrodes 114 may additionally be distal to the implant body 100. In other variations, the set of secondary electrodes 114 may be attached and exterior to the implant body 100 (e.g. the metal casing implemented as a secondary electrode). Secondary electrodes 114 may comprise of first set of electrodes 116 and/or second set of electrodes 118. The set of secondary electrodes 114 may function as a charge counterbalance to the charge generated by primary electrodes 112. For example, if the set of primary electrodes 112 generate a net negative charge to induce osteoinduction, the set of secondary electrodes 114 may generate a net positive charge to balance the primary electrodes 112 and act as a current "source" to the primary electrode "sink". Accordingly, if, for example, 1 µA of current is sinked by one set of electrodes constituting a plurality of electrodes utilized in a system, then 1 µA of current simultaneously needs to be sourced by the remaining electrodes constituting a plurality of electrodes utilized in that system (conservation of charge). In some preferable variations, the surface area of the set of secondary electrode is of similar size as compared to the surface area of the set of primary electrodes 112. Alternatively, the surface area of the set of secondary electrodes 114 may be smaller or larger than the surface area of the set of primary electrodes 112.

As secondary electrodes 114 are positioned distal to the bone growth region, there is some flexibility in how they may be implemented in the system. In some variations, secondary electrodes 114 comprise a single (possibly larger) electrode with an exposed region far from the implant body 100. This secondary electrode may have a region embedded in the implant body 100, but may alternatively not have an embedded region. In a second variation, the system may comprise multiple secondary electrodes 114 along the exterior of the implant body 100. This may particularly be the case for larger implants wherein the bone growth region resides only in the internal cavity of the implant body 100. In a third variation, wherein the system has multiple bone growth regions, that may additionally vary over time; the system may include a set of secondary electrodes 114 wherein only a subset of the secondary electrodes actively function as secondary electrodes at any one given time. For example, where secondary electrodes 114 are along the exterior surface of the implant body 100, exposed to healthy bone tissue; the active set of secondary electrodes (i.e. subset of secondary electrodes) may vary (e.g. cycle around the implant body) over time such that osteolysis is not induced in the healthy bone tissue.

It should be noted that the designation of primary electrodes 112 and secondary electrodes 114 describes a relative proximity of electrodes to a bone growth region, and thus their most likely intended utilization. Generally speaking, primary electrodes 112 and secondary electrodes 114 may have the same functional capabilities; although these capabilities may be limited by the size, shape, material construction, and location of the electrode. A subset of primary electrodes 112 may function as cathodes while another subset of primary electrodes may function as passive (neither sourcing nor sinking current), and another subset of primary electrodes may function as anodes (e.g. to induce osteolysis), wherein any of the subsets of primary electrodes may contain, all, some, or no electrodes. Similarly, a subset of secondary electrodes 114 may function as cathodes, while another subset of secondary electrodes may function as passive, and another subset of secondary electrodes 114 may function as anodes. Any subset of secondary electrodes 114 may contain zero, some, or all secondary electrodes. As mentioned previously, secondary electrodes 114 may contain a polarity to counter-balance the primary electrodes 112. Alternatively, the set of secondary electrodes 114 may have another polarity (or no polarity) for other functions. Alternatively, the set of secondary electrodes 114 may counterbalance the set of primary electrodes 112 (or a subset of primary electrodes) to a greater or lesser degree (e.g. a time average). In preferred variations, the functionality of electrodes in each set of primary and secondary electrodes may be changed dynamically as seen necessary. Alternatively, the functionality of electrodes in each set of primary electrodes 112 and/or set of secondary electrodes 114 is fixed. Alternatively, a subset of primary and/or secondary electrodes 114 may have a fixed functionality.

Primary electrodes 112 may comprise of first set of electrodes 116 or second set of electrodes 118. Dependent on the positioning of the primary electrodes 112 in the bone growth region, primary electrodes may be thus composed of a single material to optimize osteoinduction, a single material to optimize osteolysis, or may be comprised of multiple materials for optimized functionality in both. Also dependent on the precision required in the bone growth region, two-layer functionality electrodes may enable very localized bone growth activity.

Secondary electrode may comprise of the first set of electrodes 116 and/or the second set of electrodes 118. Typically, secondary electrodes 114 have a predetermined functionality, which is dependent on the main functionality of the implant and the positioning of the secondary electrodes 114. In this manner, secondary electrodes preferably comprise electrode composed of a single material. For the preferred variation wherein bone growth is desired, secondary electrodes 114 will typically function as anodes. Dependent on the positioning of the secondary electrodes 114, the material type of the secondary electrode may be chosen to minimize the anode effects of osteolysis (e.g. platinum), or maximize the anode effects of osteolysis (e.g. titanium).

Figure 2:
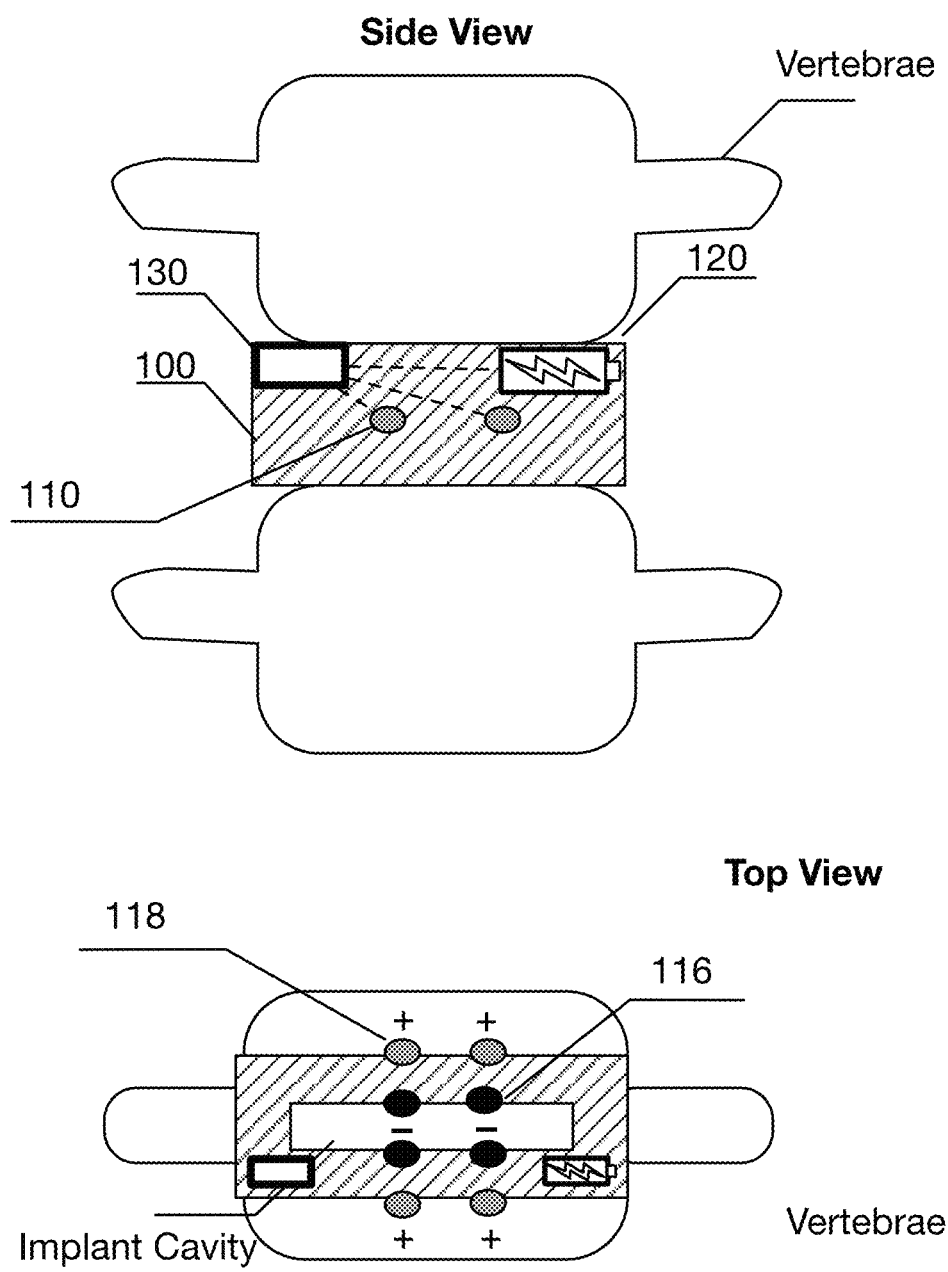
FIG. 2 is a second schematic representation of a system of a preferred embodiment.

In some preferred variations, the region of desired bone growth is the implant body 100. In one example, the entire set of primary electrodes 112 function primarily as cathodes and the entire set of secondary electrodes 114 function as anodes that counter-balance the primary electrodes 112. This example may induce osteoinduction in proximity to the primary electrodes 112, and/or inhibit (or reduce) osteolytic activity within proximity of the primary electrodes 112, and promote osteolysis in proximity to the secondary electrodes 114. In one variation with a potential benefit to enhance osteoinduction and reduce osteolysis, preferably the primary electrodes 112 are comprised of the first set of electrodes 116 and the secondary electrodes 114 are comprised of the second set of electrodes 118. That is, the first set of the plurality of electrodes includes exposed electrode sites proximal to a bone growth region, and the second set of the plurality of electrodes 118 includes exposed electrodes distal to the bone growth region. In one implementation of this example, the set of secondary electrodes 114 comprises a single electrode that is the metal casing outside of the implant body 100, as shown in FIG. 1. In another implementation of this example, the set of secondary electrodes 114 are four electrodes along the exterior surface of the implant body 100, as shown in FIG. 2. Alternative implementations of the secondary electrode in the above example may include, but are not limited to, the set of secondary electrodes 114 being a ring outside of the implant body or the set of secondary electrodes 114 being two electrode bodies at opposite poles of the implant body 100. The set of secondary electrodes 114 may, additionally or alternatively be any shape, and/or size, desired.

Figure 11:
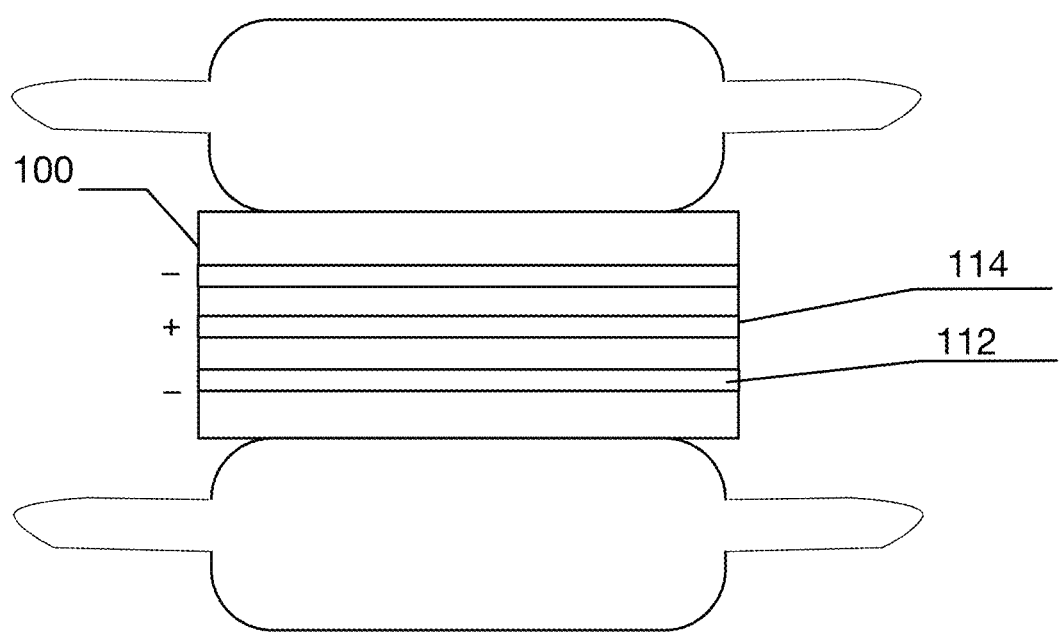
FIG. 11 is an alternate schematic representation of a system of preferred embodiment.

In another preferred example, as shown in FIG. 11, primary electrodes 112 are incorporated as rings (or other preferred shapes) on the upper and lower regions of the implant body 100 internal cavity, while a secondary electrode ring is implemented in between the two primary electrodes 112 rings. The secondary electrode ring may function as an anode, while the primary electrode rings are cathodes to induce osteoinduction directly above and below themselves to ensure osteoinduction in the endplate regions (e.g. to help fuse the implant body with the vertebrae directly above and below the implant body) In other preferred examples, the primary electrodes 112 and secondary electrodes 114 may be moved closer or further apart to change the size and location of the bone growth region and to alter the containment of osteolysis. Additionally or alternatively, polarity of the electrodes may be changed or turned off as deemed fit for bone growth. In a related approach, the secondary electrode could be configured as an anode and be a large surface plate and a set of primary electrodes 112 could be configured as cathodes and can be positioned so as to circumscribe the secondary electrode so as to contain the region of osteolysis.

The arrangement, shape, form and/or other physical properties of the first set of electrodes 116 and the second set of electrodes 118 be set into a configuration for biased stimulation in and around the implant. Here, biased implies that tissue in and around the implant would receive proportionally more charge as compared to unbiased regions. Particularly, incorporating distinct sets of electrodes (first set, second set, etc.) in the composition of primary and secondary electrodes 114 may play a significant role in biased stimulation. Additionally, through different operation modes, these biased regions of functionality may be changed over time; both to balance negative or positive effects of stimulation, and to take into account for changes in local tissue development (e.g. bone growth).

The control system 120 of a preferred embodiment may function to control the charge amplitude and polarity of the plurality of electrodes no. The control system preferably includes a processor and circuitry to connect to the plurality of electrodes 110. The control system 120 may additionally control, sync, and/or operate other components as deemed necessary. In some preferred implementations, wherein electrodes have multiple functionalities (e.g. dual activity circuit electrodes), the control system preferably controls and changes these functionalities. The control system 120 preferably controls the dynamic and multi-operating modes of the electrodes, either as distinct electrodes or as subsets of electrodes. The control system 120 may be implanted, as part of the implant body 100 or as a distinct system entity; may be located outside of the body; or may include a combination of implantable and non-implantable components.

The control system 120 preferably includes a processor allowing it to control each individual electrode distinctly, and/or subsets of electrodes as one group. The control system 120 may function autonomously, but may additionally, or alternatively, be controlled by a user through an external remote control device or communication system. In one implementation, where the implant body 100 is non-conductive, the control system 120 may allow current to be only applied at the surface of the electrode sites, thus allowing the distribution of current density to be controlled by the placement of the electrodes as well as their state during stimulation. Alternatively, the electrodes can be conductively isolated from a subset of the other electrodes and more preferably conductively isolated from each of the set of electrodes such that each electrode could be independently controlled such that current density may be similarly controlled by the control system 140.

The control system 120 preferably includes circuitry effectively connecting the control system with other system components. In preferred variations this includes the plurality of electrodes no. Additionally the circuitry may connect to the implant body 110, power system 130, or any other desired component. Circuitry may be "wired" or wireless.

The system preferably has multiple operating modes wherein the control system 130 is configured to activate the plurality of electrodes 110 to function in specific ways. Preferably, the system includes at least a stimulation operating mode, and a monitoring operating mode. In some preferred variations, the system may include a switching operating mode. The system may additionally include other operating modes (e.g. a calibration operating mode). Operating modes may function simultaneously, or distinctly, within the entire system and/or within each system subcomponent. For example in one preferred implementation, the control system 130 may activate a subset of the plurality of electrodes 110 to operate in a stimulation mode, and activate another subset of electrodes to function in a monitoring mode.

The system is preferably configured to operate in a stimulation mode. In a stimulation mode, control system 120 is configured to activate a subset of the plurality of electrodes 110 to send current through tissue to induce either osteoinduction or osteolysis in the tissue as desired. Depending on how the system is implemented, the stimulation mode may enable different types of functionalities.

In one example of a stimulation operation mode, the control system 120 activates a subset of primary electrodes 112 to function as a sink, to induce osteoinduction in a bone growth region; and activates a subset of secondary electrodes 114 to as the current source.

In a similar example, the activity of the primary electrodes 112 is not changed, but the control system 120 changes the subset of secondary electrodes 114 designated as the current source (e.g. so as not to induce significant amounts of osteolysis in surrounding tissue). In one implementation, wherein the secondary electrodes 114 are positioned at exposed sites along the exterior surface of the implant body 100; the control system 120 may cycle through active subsets of secondary electrodes 114, such that, over time, the subset of active electrodes circumnavigates the implant body 100. This type of switching behavior may enable the changing of the position of the active secondary electrode(s) 114. In some cases, there may be no one ideal location for the secondary electrode and so changing position may promote more desired bone growth. For example an anode may typically induce osteolytic effects in bone tissue, but a transient cyclical anode may ameliorate this effect.

In a third example, wherein both osteoinduction and osteolysis is desired, the control system 120 may activate a subset of primary electrodes 112 to function as current sinks in one bone growth region to induce osteoinduction, and activate another subset of primary electrodes to function as current sources in another bone growth region to induce osteolysis; and activate a subset of secondary electrodes 114 to balance the current as required. In one implementation of this example, the two bone growth regions are completed isolated, such that the control system may activate two subsets of secondary electrodes 114 to counter balance both subsets of primary electrodes. In another implementation, the two subsets of primary electrodes 112 are connected and the subset of secondary electrodes 114 counterbalances the net charge of both subsets of primary electrodes 112.

In a fourth example, wherein the plurality of electrodes 110 include electrodes composed of both titanium and platinum; the control system 120 may activate a subset of electrodes to induce bone growth, wherein the platinum section of the electrode functions as a current sink and the titanium section of the electrode functions as a current source.

In a fifth example, wherein a primary electrode is a circuit composed of two materials conductively coupled to parallel circuits switchable by a switch; the control system may switch between activating of the different materials. The control system may initially activate the platinum wire region to function as a cathode to induce osteoinduction, but later switch to the titanium wire region and activate the titanium wire to function as an anode to induce osteoinduction.

In preferred variations, the system also includes a monitoring mode. In the monitoring mode, the control system 120 is configured to utilize electrodes to determine tissue composition. In the monitoring mode, the control system may activate and current through pairs of electrodes thereby measuring the impedance in the tissue between the pair of electrodes.

In this manner, the monitoring mode may be used to monitor the bone growth within the bone growth region. Preferably, monitoring bone growth involves the control system 120 driving AC signals between pairs of electrode and thus through the intermediary tissue. By measuring the impedance, through the tissue, the relative tissue composition (i.e. amount of bone growth) may be determined. By using this measurement between electrode pairs located on the outside perimeter of each bone growth region, the control system 120 may generate an impedance profile of the entire region. In the application of spinal fusion, the impedance profile can be used to monitor the degree of bone growth, and thus spinal fusion achieved. In preferred variations, the monitoring mode is used to measure and monitor bone growth. The monitoring mode may be used in conjunction with the stimulation mode to monitor bone growth activity and then alter the bone growth activity as desired; either automatically or after physician approval.

To facilitate high level monitoring through impedance measurements, the implant may include implant bone growth monitoring circuitry which functions to measure bone growth through impedance measurements of through the monitoring mode. Bone monitoring in this manner may be beneficial in reducing dependence on more complicated, slow, and expensive monitoring techniques such as MRI, ultrasound or x-rays conducted at a healthcare facility. The optional implant bone growth monitoring circuitry can be used to measure the impedance of the tissue between pairs of one or more electrodes.

The power system 130 of a controlled embodiment functions to give power to charge the plurality of electrodes no. The power system 130 preferably includes a power source and circuitry to transmit the power to the plurality of electrodes no. The power system 130 may further power any additional components that require power. The power system may comprise of any general power source, or a multitude of power sources (e.g. electrical outlet, internal generator), but may comprise of a battery (or several batteries). The power system may alternatively, be powered through wireless power coupling or other suitable forms of remote power delivery. The power system may be implanted, as part of the implant body 100 or as a distinct system entity; may be located outside of the body; or may include a combination of implantable and non-implantable components. The power system may be connected to each electrode through wiring, or may alternatively charge electrodes through induction or other means. In some variations the power system may comprise of an external electrical source. External wiring may then be used to connect the power source to the implant body 100. Alternatively, the power system may have a transmitter placed on, or near, the patient's body that can induce power into the implant body 100 and electrodes.

In some variations, the system may additionally include a communication system. The communication system functions to allow communication between internal implanted components and external components. The communication system may allow giving input to the electrodes through the control system 140. The communication system may additionally or alternatively allow for additional exchanges of command and/or data. For example, the communication system may send information about the generated fields from the electrodes to an external source. The communication system may be a hardwired system that physically connects external and internal components, but will preferably be a wireless system. The wireless system may function over resonant inductive coupling, RF irradiation, IR ultrasound or any other wireless medium.

The following section provides sample preferred implementations of the system with the commonly used spinal cage implants described previously. As these examples are in no way exhaustive, examples described for one implant body 100 may be combined or exchanged with another implant body implementation as desired.

As show in FIG. 5, the ALIF cage is a spinal cage that may be implanted from the anterior side. As a "larger" implant, the ALIF cage preferably has only a bone growth region in the internal cavity of the implant body 100. For this variation, the primary electrodes 112 may be along the interior surface of the ALIF implant body 100, while secondary electrodes 114 are along the exterior perimeter of the implant body 110. In one preferred example, primary electrodes 112 include four electrodes exposed along the internal cavity (e.g. two electrodes along the posterior interior surface and two electrodes along the anterior interior cavity surface); and secondary electrodes 114 include four electrodes exposed on the exterior surface (e.g. two electrodes on the anterior surface and two electrodes on the posterior surface of the implant body 100). In one implementation, as shown in FIG. 5, the primary electrodes 112 are a first set of electrodes 116 composed of platinum, and the secondary electrodes 114 are a second set of electrodes 118 composed of titanium.

In an alternative variation, the ALIF cage may additionally include a bone growth region on the anterior side of the implant body 100. In this variation, primary electrodes 112 may additionally be along the anterior exterior surface of the implant body 100, while secondary electrodes 114 may then just be along the posterior exterior surface of the implant body 100. In one implementation of this alternative variation, the primary electrodes 112 and anterior electrodes on the exterior surface may be a third set of electrodes composed of both titanium and platinum for selective activity.

In some implementations, the bone growth region may be a more narrow region of the interior cavity (e.g. the bone growth region includes regions close to the upper and lower vertebrae) as shown in the schematic drawing of FIG. 11 In these implementations, the primary electrodes 112 may include a ring along the interior cavity close to the top surface of the implant body 10o and a ring along the bottom surface of the interior cavity close to the adjacent lower vertebrae. Secondary electrodes 114 may comprise an internal ring as shown in FIG. 11, or may alternatively comprise of electrodes exterior to the implant body 10o as described in other variations.

In some variations the secondary electrodes 114 external to the spinal region (anterior side) may comprise a metal casing, or conductive attachment extending from the spinal cord region.

As shown in FIG. 6, the lateral cage is another typically implemented spinal cage. The lateral cage is an implant body 100 with a large variance in size, and thus potentially large variance in implementation. In preferred variations, the lateral cage may only have a bone growth region in the interior cavity of the implant body 100. For this variation, the primary electrodes 112 may be along the interior surface of the lateral cage, while secondary electrodes 114 are along the exterior perimeter of the lateral cage. In one preferred example, as shown in FIG. 2, primary electrodes 112 include four electrodes exposed along the interior surface (e.g. two electrodes along the posterior interior surface and two electrodes along the anterior interior surface; and secondary electrodes 114 include four electrodes exposed on the exterior surface (e.g. two electrodes on the anterior surface and two electrodes on the posterior surface of the implant body 100). In one implementation all primary electrodes 112 function as cathodes to induce bone growth, while all secondary electrodes 114 function simulataneously as anodes. In this implementation, the four primary electrodes 112 are a first set of electrodes 116 composed of platinum, and the four secondary electrodes 114 are a second set of electrodes 118 composed of titanium.

In a second implementation all primary electrodes 112 function as cathodes, while only a single secondary electrode 114 functions as anode at any given time. Over time, the active secondary electrode, functioning as the anode, cycles through all secondary electrodes to potentially minimize the osteolysis effects of the anode.

In a second variation, the system may include the primary electrodes along the interior surface of the implant body to induce bone growth, but alternatively the secondary electrodes 114 includes a single electrode distal to the bone growth region. In one example, the implant body 100 includes a metal casing, wherein the single secondary electrode is the metal casing of the implant body, as shown in FIG. 1. In a second example, the single secondary electrode 114 comprises an electrode on the "nose" of the implant body (i.e. the opposite side as the metal casing) as shown in FIG. 7.

In a third variation, the system may further include a bone growth region on the posterior exterior of the implant body 100. This exterior bone growth region outside of the implant body 100 may be to reduce bone growth in soft tissue. In this variation, the set of primary electrodes 112 includes electrodes along the interior surface and along the posterior, exterior surface of the implant body 100; and the set of secondary electrodes 114 includes electrodes along the exterior perimeter of the spinal cage, excluding the posterior surface of the implant body. In this variation, the primary electrodes 112 in the interior function primarily as cathodes, to induce bone growth; while the primary electrodes on the posterior surface function primarily as anodes (although occasionally as cathodes), to reduce bone growth on the posterior side of the implant body; and the secondary electrodes 114 may then function primarily as anodes to balance the required charge of the primary electrodes 112. In one implementation of this third variation, as shown in FIG. 6, the primary electrodes 112 that vary functionality may comprise a first set of electrodes 116 composed of two materials, one to optimize osteoinduction and one to optimize osteolysis; the primary electrodes 112 along the interior surface of the implant body 100 may comprise a second set of electrodes 118, composed of a second material to optimize osteoinduction; and the secondary electrodes along the exterior surface may also be a second set of electrodes 118, or even a third set of electrodes, distinct from the first set of electrodes and the second set of electrodes.

As shown in FIG. 10, the TLIF cage is another typically implemented spinal cage. The TLIF cage is an implant body 100 that is of "smaller" size, such that multiple TLIF cages may be implanted between a pair of vertebrae.

In one preferred variation, a single TLIF cage is implanted within the spinal region. In one example, wherein the TLIF cage is implanted fairly central in the spinal region, the bone growth region may include the interior cavity and the exterior region adjacent to the TLIF cage. In this example, primary electrodes 112 may be along both the interior surface and exterior surface of the implant body. In one implementation, secondary electrodes 114 may also be along the exterior surface of the TLIF cage. In this implementation, the control system 120 may activate the cyclical switching behavior of subsets of secondary electrodes 114 to prevent/reduce osteolysis in the exterior. In this implementation, the active subset of secondary electrodes 114 may change and circumnavigate the exterior surface of the implant body 100 to prevent significant bone loss in one region, enabling net bone growth external to the implant body 100.

In a second example of this variation, the secondary electrode may comprise a single electrode extending out in one location from the implant body 100. This single electrode may lead to bone loss (or less bone growth) in that one region, with preferably little significant effect on other bone growth regions. In one implementation, wherein the TLIF cage is positioned such that the shorter end of the cage is pointing to the periphery of the spinal column, the secondary electrode 114 may be on the shorter end. In many implementations, less bone growth is needed as compared to other regions, positioning the secondary electrode 114 on the shorter end may thus minimize the significance of potential bone breakdown as compared to other regions. In a second implementation of this second example, as shown in FIG. 10, the primary electrodes 112 comprise a first set of electrodes 116 composed of a material to optimize osteoinduction, while the secondary electrode comprises a second set of electrodes 118 composed of a material to minimize osteolysis.

In a second preferred variation, multiple TLIF cages (e.g. two TLIF cages) are implanted between a pair of vertebrae. In one example of this variation the two cages are fairly interior along the spinal column and this example functions similarly to the first variation.

In a second example of the second variation, the TLIF cages are implanted such that one side of each implant body is exterior to the bone growth region (e.g. outside of the spinal column). In this example, the system includes secondary electrodes 114 only along the exterior surface of the TLIF cage outside of the bone growth region, while the exterior surface of the implant body 100 within the bone growth region would include primary electrodes 112 along with the primary electrodes 112 within the implant body. In one implementation of this second example, since the secondary electrodes 114 are exterior to a region of any desired bone growth, the primary electrodes 112 and secondary electrodes 114 comprise a first set of electrodes 116 composed of platinum, to optimize osteoinduction for the primary electrodes 112 with no negative results due to "better" osteolysis outside of the region for bone growth.

As shown in FIG. 9, the PLIF cage is another typically implemented spinal cage. The PLIF cage is an implant body 100 that is of "smaller" size, such that multiple PLIF cages may be implanted between a pair of vertebrae. As with the TLIF cage, a single PLIF cage or multiple PLIF cages may be implanted between each vertebra. Although insertion of the PLIF cage is from the posterior, implementations of the PLIF cage may be similar to the TLIF cage.

In one preferred variation, a single PLIF cage is implanted within the spinal region. In one example, wherein the PLIF cage is implanted fairly central in the spinal region, the bone growth region may include the interior cavity and the exterior region adjacent to the PLIF cage. In this example, primary electrodes 112 may be along both the interior surface and exterior surface of the implant body 100. In one implementation, secondary electrodes 114 may extend outwards from the exterior surface of the PLIF cage. In this implementation, the secondary electrodes 114 may extend sufficiently such that they don't affect the bone growth region. As per the TLIF implementation, and shown in FIG. 9, the primary electrodes 112 and the secondary electrodes 114 comprise a first set of electrodes 116, since the secondary electrodes 114 are outside of the desired bone growth region and thus bone growth agnostic.

In a second example of this variation, the secondary electrode may comprise a single electrode extending out in one location from the implant body 100. This single electrode may lead to bone loss (or less bone growth) in that one region, with preferably little significant effect on other bone growth regions. In one implementation of this second example, this single secondary electrode comprises a secondary electrode composed of a material to minimize osteolysis.

In a second preferred variation, multiple PLIF cages (e.g. two PLIF cages) are implanted between a pair of vertebrae. In one example of this variation, the two cages are fairly interior along the spinal column and this example functions similarly to the first variation.

In a second example of the second variation, the PLIF cages are implanted such that one side of each implant body is exterior to the bone growth region (e.g. outside of the spinal column). In this example, the system includes secondary electrodes 114 only along these exterior surfaces of the PLIF cages outside of the bone growth region. The exterior surface of the implant body 100 within the bone growth region would include primary electrodes 112 along with the primary electrodes within the implant body 100. In one implementation of this second example of the second variation, the primary electrodes 112 in between the two implants comprise a first set of electrodes 116 composed of two materials, and the primary electrodes in the interior of the PLIF cages and the secondary electrodes 114 comprise a second set of electrodes 118. In this implementation, the primary electrodes in between the two implants may be in regions of desired bone growth and bone breakdown (e.g. on the anterior side of the spinal column), and are preferably composed of two materials to optimize both bone growth and bone breakdown. The primary electrodes within the implant body 100 (second set electrodes) are preferably composed of a material to optimize bone growth. And the secondary electrodes 114 (also second set electrodes) are outside of the bone growth region, thus bone growth agnostic, and composed of the same material as the interior primary electrodes.

The ACF cage is another typically implemented spinal cage. The ACF cage may be a significantly smaller spinal cage wherein a single spinal cage is implanted between cervical vertebrae. Although typically much smaller, the ACF cage may have similar implementations as described for the ALIF cage.

In one preferred variation, the bone growth region of the ACF cage is the interior cavity of the implant body 100. For this variation, the primary electrodes 112 may be along the interior cavity of the ACF implant body 100, while secondary electrodes 114 are along the exterior perimeter of the implant body. In one implementation of this variation, the primary electrodes comprise a first set of electrodes 116 composed of a material to optimize osteoinduction, and the secondary electrodes 114 comprise a second set of two-layer electrodes. Generally, these secondary electrodes 114 preferably utilize a material to minimize osteolysis, but may also utilize a different material to promote osteolysis to prevent bone growing in soft tissue.

3. Method

As shown in FIG. 15, a method for altering bone growth on and within an orthopedic implant of a preferred embodiment includes: providing a plurality of electrodes with the electrodes made of at least two material constructions S110, positioning the electrodes S120, creating a polarity within a subset of the electrodes S130. The method may function to create preferred regions of osteolysis and osteoinduction as desired by the polarity and positioning of the electrodes with respect to the implant. The method is preferably implemented with a system as described above, but may be implemented with any suitable alternative system.

Block S110, which includes providing a plurality of electrodes with the electrodes made of at least two material constructions, functions to configure a pattern of electrode types used for electrical stimulation during osteoinduction and/or osteolysis. Providing a plurality of electrodes S110 may include selecting or specifying electrodes with respect to their shape and construction. Electrode shape may affect the impedance of the electrode, and the shape of the electric field created when the electrode is sourcing or sinking current. Electrode material type may also affect electrode impedance, and may additionally affect bone growth functionality. For example distinct platinum electrodes used as both electro-negative electrodes and electro-positive electrodes may induce osteoinduction in proximity of both the positively charged and negatively charged platinum electrode, while other material types may function to induce osteoinduction at the electro-negative electrode and osteolysis at the electro-positive electrode. Providing a plurality of electrodes S110 may additionally be fully or partially predetermined for the chosen orthopedic implant. For example a specific implants may have preconfigured electrode type and placement that is selected for that type of implant. Furthermore, the electrode configuration may be customized for individual cases or classes of cases. For example, two different configurations of electrodes may be used depending on the particular case.

Block S120, which includes positioning of electrodes, functions to set electrodes in specific spatial positions with respect to the implant where positioning of electrodes S120 may designate possible regions and rates of osteolysis or osteoinduction. Positioning of electrodes S120 may occur at different time within the method. Positioning of a subset of electrodes may or may not be dependent on the positioning of other subsets of electrodes. Positioning of a subset of electrodes may occur prior to implantation of the implant, during the placement of the implant, after the implant has already been placed within a patient, and/or any combination of the prior, during, or after. Implants may have specific design features with electrode position in mind. For examples, implants may have holes or grooves for the placement of electrodes. Thus positioning of a subset of electrodes may occur, or be determined, by the choice and/or design of the implant. Alternatively, positioning of electrodes S120 may occur as desired to induce appropriate bone growth.

In one variation, positioning of electrodes is statically set for a given implant device. In another variation, positioning of electrodes can be dynamically set during operation of the implant device by selecting subsets of electrodes for active use and/or inactive use.

Positioning of electrodes S110 may additionally be comprised of choosing the size of the electrode; as both electrode thickness and surface area have an effect on the current passed through the electrode and generated electric field. If desired, a large surface area electrode may be used as an electro-positive electrode to balance the current generated from a large number of electro-negative electrodes which may ensure a low current density at the electro-positive electrode surface and the surrounding tissue.

Positioning of electrodes S120 may additionally be dependent on the shape of the electrodes. Wire-like, and/or arbitrarily shaped, but smaller electrodes may be preferably positioned within the implant, or within the implant cavities, but may alternatively be positioned in other regions, i.e. in, on, or outside of but proximal to the implant. Disc shaped, and/or large arbitrarily shaped electrodes, may preferably be positioned exterior to the implant. Additionally and/or alternatively these larger electrodes may be positioned on or inside of the implant as is feasibly possible (e.g. large electrodes may not fit due to space).

Positioning of electrodes S120 may also be dependent of the type of electrode. Multi-material electrodes may allow greater flexibility of positioning the electrode, as different cathode and anode functionality of the electrode may allow more control over osteoinduction and osteolysis.

Block S130, creating a polarity within a subset of electrodes functions in creating electro-positive electrodes and electro-negative electrodes that induce electric fields about each charged electrode. The negative electric fields may function in promoting osteoinduction while positive electric fields may function in promoting osteolysis. Creating a polarity within a subset of electrodes S130 may be additionally dependent on the type of electrodes. That is, greater power is required to drive current between an electrode pair comprised of a materials resulting in greater overall impedance.

As a person skilled in the art will recognize from the previous detailed description and from the figures and claims, modifications and changes can be made to the embodiments of the invention without departing from the scope of this invention as defined in the following claims.

We claim:

1. A system for altering bone growth near an orthopedic implant comprising:
   an implant body, wherein the implant body comprises an exterior surface and an interior surface defining an internal cavity of the implant body;
   a plurality of electrodes, wherein each electrode is at least partially embedded in the implant body, and comprises at least:
   a first set of electrodes from the plurality of electrodes, composed of a first material, wherein at least one electrode from the first set of electrodes comprises two distinct regions, where a first distinct region is composed of the first material and a second distinct region is composed of a different material, a switch conductively coupled to the at least one electrode and configured to selectively enable current to travel through each of the two distinct regions, and a second set of electrodes from the plurality of electrodes, composed of a second material; and a control system, comprising a processor and circuitry that connects to the plurality of electrodes, wherein the processor comprises machine instructions configured to control direction and magnitude of current traveling through each electrode from the plurality of electrodes; and a power system comprising a power source and circuitry that provides electrical power for function of the plurality of electrodes.

2. The system of claim 1, wherein the implant body is a spinal cage, and the plurality of electrodes include:

a subset of the electrodes composed of the first material that are partially embedded in the spinal cage and partially exposed at electrode sites on the interior surface of the spinal cage, and a subset of electrodes composed of the second material that are partially embedded in the spinal cage and partially exposed at electrode sites on the exterior surface of the spinal cage.

3. The system of claim 1, wherein the first material is platinum.

4. The system of claim 3, wherein the second material is titanium.

5. The system of claim 1, wherein the at least one electrode comprises circuitry configured to enable opposite currents to flow through the first and second distinct regions of the electrode thereby creating an electric field at the exposed electrode site of the electrode that promotes bone growth.

6. The system of claim 1, wherein the first material comprises platinum and the different material comprises titanium.

7. The system of claim 1, wherein each electrode from the first set of electrodes is a two-layer wire comprising:

a central cylindrical layer composed of the first material, and a hollow cylindrical layer surrounding the central cylindrical layer, composed of the different material.

8. The system of claim 1, wherein each electrode from the first set of electrodes further comprises multiple distinct regions, wherein each additional region is composed of a material distinct from all regions adjacent to the additional region.

9. The system of claim 8, wherein each electrode from the first set of electrodes is a multi-layer wire, comprising:

a central cylindrical layer composed of the first material;

a second cylindrical layer surrounding the central cylindrical layer, composed of the different material; and at least one additional hollow cylindrical layer surrounding the second cylindrical layer, composed of a distinct material as compared to the second cylindrical layer.

10. The system of claim 9, wherein each alternating layer after the central cylindrical layer comprises an insulating layer composed of electrically insulating material.

11. The system of claim 8, wherein the electrode with multiple distinct regions is a multi-layer sheet, comprising:

a flat sheet composed of the first material, a flat sheet composed of the different material stacked upon the first material; and at least one additional flat sheet layer stacked upon a prior flat sheet, wherein the additional flat sheet layer is composed of a distinct material as compared to its prior flat sheet.

12. The system of claim 1, wherein each electrode comprises a two-layer conducting sheet, comprising a flat sheet composed of the first material and a flat sheet composed of the different material.

13. The system of claim 1, wherein each electrode comprises a circuit component with a switch, such that the first material region and the different material region of the electrode are parallel components of the circuit, and the switch enables current to selectively flow only through one of the two regions.

14. The system of claim 1, wherein the first set of electrodes from the plurality of electrodes includes exposed electrode sites proximal to a bone growth region, and the second set electrodes from of the plurality of electrodes includes exposed electrode sites distal to the bone growth region.

15. A system for altering bone growth near an orthopedic implant comprising:

an implant body, wherein the implant body comprises an exterior surface and an interior surface defining an internal cavity of the implant body;

a plurality of electrodes, wherein each electrode is at least partially embedded in the implant body, and comprises at least:

a first set of electrodes from the plurality of electrodes, composed of a platinum, wherein at least one electrode from the first set of electrodes further comprises two distinct regions, wherein the electrode further comprises a first material region composed of the platinum and a distinct second material region composed of a different material, wherein the at least one electrode further comprises a switch conductively coupled to the at least one electrode selectively allowing current to travel through an electrode region, and a second set of electrodes from the plurality of electrodes, composed of a titanium; and a control system, comprising a processor and circuitry that connects to the plurality of electrodes, wherein the processor comprises machine instructions configured to control direction and magnitude of current traveling through each electrode from the plurality of electrodes; and a power system comprising a power source and circuitry that provides electrical power for function of the plurality of electrodes.

16. The system of claim 15, wherein the first material region and the distinct second material region of the electrode are parallel components of the circuit, and the switch enables current to selectively flow only through one of the two regions.

17. The system of claim 15, wherein the first set of electrodes includes exposed electrode sites proximal to a bone growth region, and the second set of electrodes includes exposed electrode sites distal to the bone growth region.

* * * * *